(12) United States Patent
Fessmann et al.

(10) Patent No.: US 7,250,063 B2
(45) Date of Patent: Jul. 31, 2007

(54) DIAMINOPYRAZOLE DERIVATIVES AND THEIR USE FOR OXIDATION DYEING OF KERATINOUS FIBRES

(75) Inventors: Thilo Fessmann, Aulnay sous Bois (FR); Eric Terranova, Magagnosc (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/433,683

(22) PCT Filed: Nov. 29, 2001

(86) PCT No.: PCT/FR01/03778

§ 371 (c)(1),
(2), (4) Date: Dec. 3, 2003

(87) PCT Pub. No.: WO02/46165

PCT Pub. Date: Jun. 13, 2002

(65) Prior Publication Data

US 2004/0083558 A1    May 6, 2004

(30) Foreign Application Priority Data

Dec. 6, 2000 (FR) .................................. 00 15837

(51) Int. Cl.
*A61K 7/13* (2006.01)
(52) U.S. Cl. .................. 8/405; 8/406; 8/409; 8/410; 8/412; 8/423; 8/568; 8/570; 8/579; 548/302.7
(58) Field of Classification Search ............. 8/405, 8/406, 409, 410, 411, 412, 423, 568, 570, 8/579; 548/302.7
See application file for complete search history.

(56) References Cited

U.S. PATENT DOCUMENTS

| | | |
|---|---|---|
| 5,534,267 A | 7/1996 | Neunhoeffer et al. ...... 424/701 |
| 5,663,366 A | 9/1997 | Neunhoeffer et al. .... 548/371.4 |
| 5,865,855 A * | 2/1999 | Doehling et al. .............. 8/409 |
| 6,099,592 A | 8/2000 | Vidal et al. ..................... 8/409 |

FOREIGN PATENT DOCUMENTS

| | | | |
|---|---|---|---|
| DE | 196 43 059 | | 4/1998 |
| DE | 196 46 609 | | 5/1998 |
| DE | 20013156 | U1 * | 10/2000 |
| WO | WO00/43367 | | 7/2000 |

OTHER PUBLICATIONS

STIC Search Report dated Jan. 5, 2005.*

* cited by examiner

*Primary Examiner*—Eisa Elhilo
(74) *Attorney, Agent, or Firm*—Steptoe & Johnson LLP

(57) ABSTRACT

The invention concerns novel diaminopyrazole derivatives of formula (I), wherein: $R_1$ represents $C_1$-$C_6$ alkyl or $C_2$-$C_6$, preferably up to $C_4$, alkenyl, linear or branched, bearing at least a substituent selected among OR, NHR, NRR', SR, $SO_2R$, COOH, $CONH_2$, CONRR', $PO(OH)_2$, SH, $SO_3X$, a non-cationic heterocycle, Cl, Br or I⁻; X represents H, Na, K or $NH_4$; R and R', identical or different, represent $C_1$-$C_6$ alkyl or $C_2$-$C_6$, preferably up to $C_4$, alkenyl, linear or branched, unsubstituted or substituted by one or several functional groups selected among OH, $NH_2$, OR, NHR, NRR', SR, SOR, $SO_2R$, COOH, $CONH_2$, CONRR', PO $(OH)_2$, SH, $SO_3X$, a non-cationic heterocycle, Cl, Br or I, X, R and R' having the definitions mentioned above; $R_2$ represents H, or $C_1$-$C_6$ alkyl or $C_2$-$C_6$, preferably up to $C_4$, alkenyl, linear or branched, unsubstituted or substituted by one or several functional groups selected among OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X, R and R' having the definitions mentioned above; and their physiologically acceptable salts, and their use for oxidation dyeing of keratinous fibres, in particular human hair.

24 Claims, No Drawings

DIAMINOPYRAZOLE DERIVATIVES AND THEIR USE FOR OXIDATION DYEING OF KERATINOUS FIBRES

The present invention relates to novel diaminopyrazole derivatives, to a composition for the oxidation dyeing of keratin fibers, and in particular of human keratin fibers such as the hair, comprising at least one diaminopyrazole derivative as oxidation base, and to the oxidation dyeing processes using it.

It is known practice to dye keratin fibers, and in particular human hair, with dye compositions containing oxidation dye precursors, in particular ortho- or para-phenylenediamines, ortho-aminophenols or para-minophenols and heterocyclic compounds such as diaminopyrazole derivatives, which are generally referred to as oxidation bases. The oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or coloration modifiers, the latter being chosen in particular from aromatic meta-diamines, meta-minophenols, meta-diphenols and certain heterocyclic compounds.

The variety of molecules used as oxidation bases and couplers makes it possible to obtain a wide range of colors.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must allow white hairs to be covered, and, lastly, they must be as unselective as possible, i.e., they must allow the smallest possible differences in coloration to be produced over the entire length of the same keratin fiber, which may indeed be differently sensitized (i.e., damaged) between its tip and its root. They must also show good chemical stability in the formulations, and must have a good toxicological profile.

Furthermore, for a certain number of applications, dyes that produce chromatic shades on the hair are desired.

Patent applications DE 42 34 885, 196 43 059 and 196 46 609 disclose 4,5-diaminopyrazole derivatives, which, when used together with various couplers, especially benzoxazines, give chestnut-brown shades with blue, red, violet, aubergine or coppery glints.

However, these dyes do not satisfy all the above requirements.

The inventors have now discovered, entirely surprisingly and unexpectedly, that it is possible to obtain dyes, which are capable of producing powerful, particularly chromatic, bright and relatively unselective colorations, which have excellent properties of resistance to the various attacking factors to which keratin fibers may be subjected, by using as oxidation base the diaminopyrazoles of the formula (I) below or physiologically acceptable salts thereof.

One subject of the present invention is thus the novel diaminopyrazoles having the following structure:

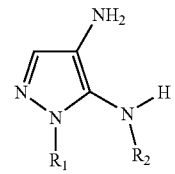

(I)

in which $R_1$ denotes a linear or branched $C_1$-$C_6$ alkyl radical or $C_2$-$C_6$, and preferably up to $C_4$, alkenyl radical, bearing at least one substituent chosen from OR, NHR, NRR', SR, SOR, $SO_2R$, COOH, $CONH_2$, CONRR', $PO(OH)_2$, SH, $SO_3X$, a non-cationic heterocycle, Cl, Br and I, X denotes H, Na, K or $NH_4$, R and R', which may be identical or different, denote a linear or branched $C_1$-$C_6$ alkyl radical or $C_2$-$C_6$, and preferably up to $C_4$, alkenyl radical, which is unsubstituted or substituted with one or more functional groups chosen from OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br and I, X, R and R' having the meanings given above, $R_2$ denotes H or a linear or branched $C_1$-$C_6$ alkyl radical or $C_2$-$C_6$, and preferably up to $C_4$, alkenyl radical, which is unsubstituted or substituted with one or more functional groups chosen from OH, $NH_2$, OR, NHR, NRR', SR, SOR, $SO_2R$, COOH, $CONH_2$, CONRR', $PO(OH)_2$, SH, $SO_3X$, a non- cationic heterocycle, Cl, Br, and I, X, R and R' having the definitions given above.

A subject of the invention is also the salts with physiologically acceptable acids or bases of the compounds of formula (I), such as the hydrochlorides, hydrobromides, sulfates, tartrates, lactates or acetates, or the salts obtained with sodium hydroxide, potassium hydroxide, ammonia, amines or alkanolamines.

A subject of the invention is also a composition for the oxidation dyeing of keratin fibers, and in particular of human keratin fibers such as the hair, characterized in that it contains, in a medium that is suitable for dyeing, as oxidation base, at least one diaminopyrazole of formula (I) above, or salts thereof with physiologically acceptable acids or bases.

As mentioned above, the colorations obtained with the oxidation dye composition in accordance with the invention are powerful, particularly bright and chromatic. They in particular produce shades that are free of or contain very little blue or yellow. Furthermore, they show excellent properties of resistance with respect to the action of various external agents (light, bad weather, washing, permanent-waving, perspiration and friction).

A subject of the invention is also a process for the oxidation dyeing of keratin fibers using such a dye composition.

As examples of diaminopyrazoles of formula (I) according to the invention, mention may be made of the compounds belonging to the following classes:

| Structure | Name | Structure | Name | Structure | Name |
|---|---|---|---|---|---|
| 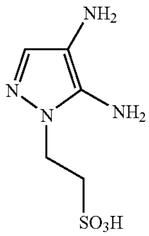 | 2-(4,5-diamino-pyrazol-1-yl)ethane-sulfonic acid | 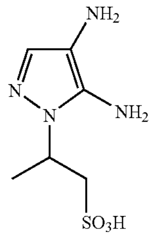 | 2-(4,5-diamino-pyrazol-1-yl)-propane-1-sulfonic acid | 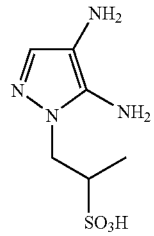 | 1-(4,5-diamino-pyrazol-1-yl)-propane-2-sulfonic acid |
| 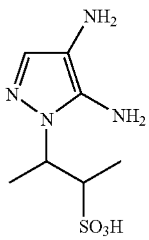 | 3-(4,5-diamino-pyrazol-1-yl)butane-2-sulfonic acid | 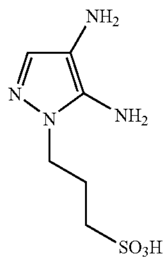 | 3-(4,5-diamino-pyrazol-1-yl)-propane-1-sulfonic acid | 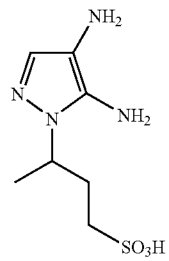 | 3-(4,5-diamino-pyrazol-1-yl)butane-1-sulfonic acid |
| 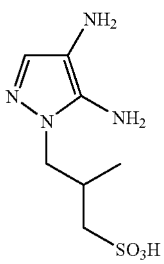 | 3-(4,5-diamino-pyrazol-1-yl)-2-methyl-propane-1-sulfonic acid | 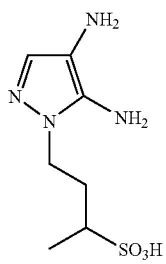 | 4-(4,5-diamino-pyrazol-1-yl)butane-2-sulfonic acid | 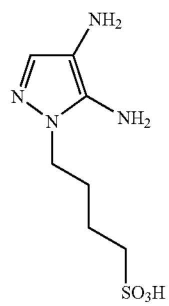 | 4-(4,5-diamino-pyrazol-1-yl)butane-1-sulfonic acid |
| 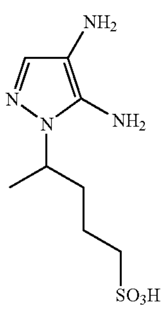 | 4-(4,5-diamino-pyrazol-1-yl)-pentane-1-sulfonic acid | 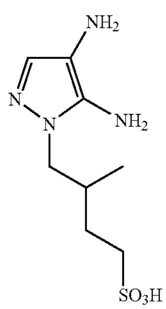 | 4-(4,5-diamino-pyrazol-1-yl)-3-methyl-butane-1-sulfonic acid | 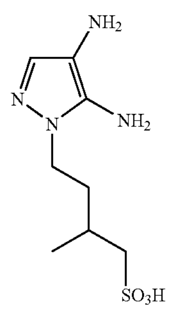 | 4-(4,5-diamino-pyrazol-1-yl)-2-methyl-butane-1-sulfonic acid |
| | 5-(4,5-diamino-pyrazol-1-yl)-pentane-2-sulfonic acid | | 5-(4,5-diamino-pyrazol-1-yl)-pentane-1-sulfonic acid | | 5-(4,5-diamino-pyrazol-1-yl)hexane-1-sulfonic acid |

-continued

| Structure | Name | Structure | Name | Structure | Name |
|---|---|---|---|---|---|
| | 5-(4,5-diamino-pyrazol-1-yl)-4-methyl-pentane-1-sulfonic acid | | 5-(4,5-diamino-pyrazol-1-yl)-3-methyl-pentane-1-sulfonic acid | | 5-(4,5-diamino-pyrazol-1-yl)-2-methyl-pentane-1-sulfonic acid |
| 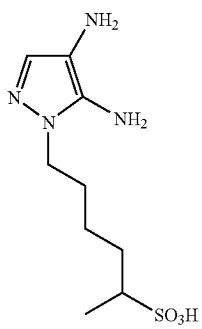 | 6-(4,5-diamino-pyrazol-1-yl)hexane-2-sulfonic acid | 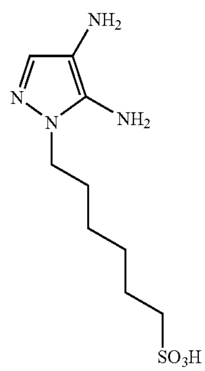 | 6-(4,5-diamino-pyrazol-1-yl)hexane-1-sulfonic acid | 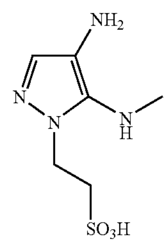 | 2-(4-amino-5-methyl-amino-pyrazol-1-yl)ethane-sulfonic acid |
| 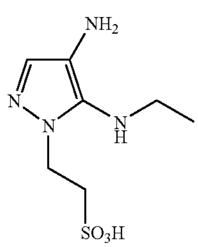 | 2-(4-amino-5-ethyl-amino-pyrazol-1-yl)ethane-sulfonic acid | 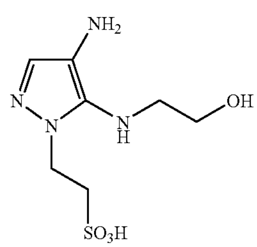 | 2-[4-amino-5-(2-hydroxy-ethylamino)-pyrazol-1-yl]ethane-sulfonic acid | 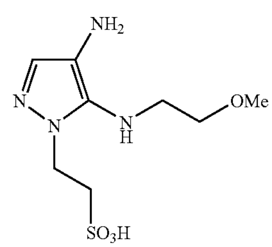 | 2-[4-amino-5-(2-methoxyethyl-amino)-pyrazol-1-yl]ethane-sulfonic acid |
| 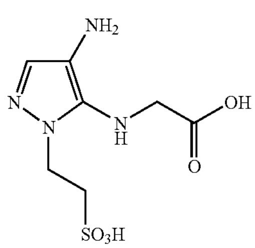 | [4-amino-2-[2-ethyl)-2H-pyrazol-3-ylamino]-acetic acid | 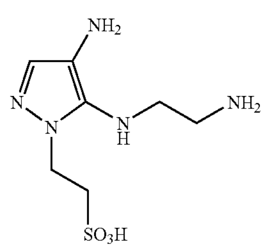 | 2-[4-amino-5-(2-amino-ethylamino]-pyrazol-1-yl]ethane-sulfonic acid | 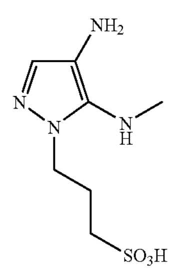 | 3-(4-amino-5-methyl-aminopyrazol-1-yl)-propane-1-sulfonic acid |
| 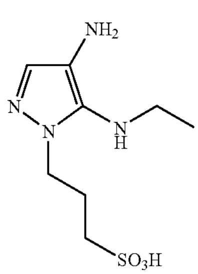 | 3-(4-amino-5-ethyl-amino-pyrazol-1-yl)-propane-1-sulfonic acid | 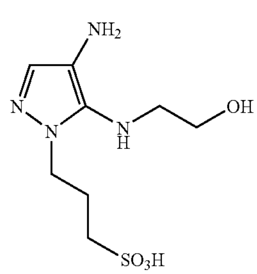 | 3-{4-amino-5-(2-hydroxy-ethyl-amino)-pyrazol-1-yl}-propane-1-sulfonic acid | 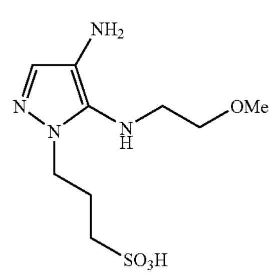 | 3-[4-amino-5-(2-methoxyethyl-amino)-pyrazol-1-yl]propane-1-sulfonic acid |

-continued

| Structure | Name | Structure | Name | Structure | Name |
|---|---|---|---|---|---|
| | [4-amino-2-(3-sulfo-propyl)-2H-pyrazol-3-ylamino]-acetic acid | | 3-[4-amino-5-(2-amino-ethylamino)-pyrazol-1-yl]-propane-1-sulfonic acid | | |
| | 2-(4,5-diamino-pyrazol-1-yl)-acetamide | | 2-(4,5-diamino-pyrazol-1-yl)propion-amide | | 3-(4,5-diamino-pyrazol-1-yl)propion-amide |
| | 3-(4,5-diamino-pyrazol-1-yl)butyr-amide | | 3-(4,5-diamino-pyrazol-1-yl)-2-methyl-propionamide | | 4-(4,5-diamino-pyrazol-1-yl)butyr-amide |
| | 4-(4,5-diamino-pyrazol-1-yl)pentan-oic acid amide | | 4-(4,5-diamino-pyrazol-1-yl)-3-methyl-butyramide | | 4-(4,5-diamino-pyrazol-1-yl)-2-methyl-butyramide |
| | 5-(4,5-diamino-pyrazol-1-yl)pentan-oic acid amide | | 5-(4,5-diamino-pyrazol-1-yl)hexanoic acid amide | | 5-(4,5-diamino-pyrazol-1-yl)-4-methyl-pentanoic acid amide |

-continued

| Structure | Name | Structure | Name | Structure | Name |
|---|---|---|---|---|---|
| 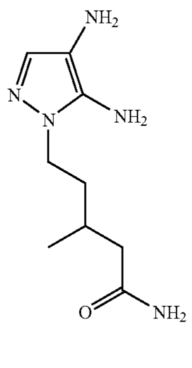 | 5-(4,5-diamino-pyrazol-1-yl)-3-methyl-pentanoic acid amide | 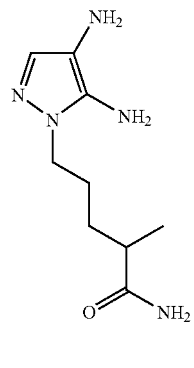 | 5-(4,5-diamino-pyrazol-1-yl)-2-methyl-pentanoic acid amide | 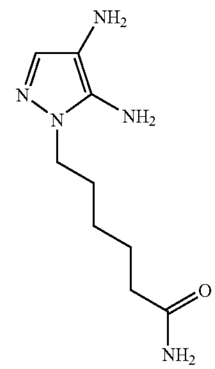 | 6-(4,5-diamino-pyrazol-1-yl)hexanoic acid amide |
| | 2-(4-amino-5-methyl-amino-pyrazol-1-yl)acet-amide | | 2-(4-amino-5-ethylamino-pyrazol-1-yl)acetamide | | 2-[4-amino-5-(2-hydroxy-ethyl-amino)pyrazol-1-yl]acet-amide |
| 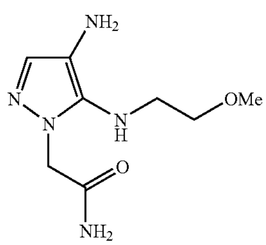 | 2-[4-amino-5-(2-methoxy-ethyl-amino)-pyrazol-1-yl]-acetamide | 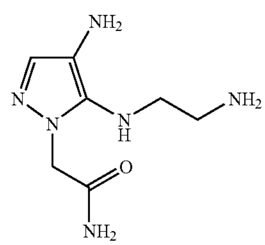 | 2-[4-amino-5-(2-amino-ethylamino)-pyrazol-1-yl]acetamide | 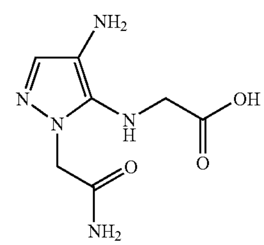 | (4-amino-2-carbamoyl-methyl-2H-pyrazol-3-ylamino)-acetic acid |
| 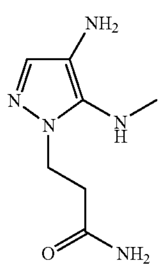 | 3-(4-amino-5-methyl-aminopyrazol-1-yl)propion-amide | 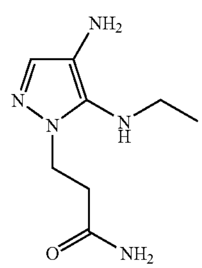 | 3-(4-amino-5-ethyl-amino-pyrazol-1-yl)propion-amide | 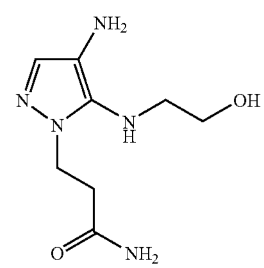 | 3-[4-amino-5-(2-hydroxy-ethyl-amino)-pyrazol-1-yl]propion-amide |
| 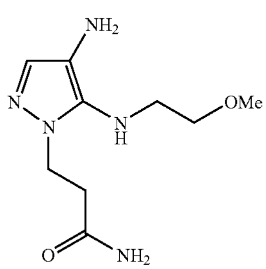 | 3-[4-amino-5-(2-methoxy-ethylamino)-pyrazol-1-yl]propion-amide | 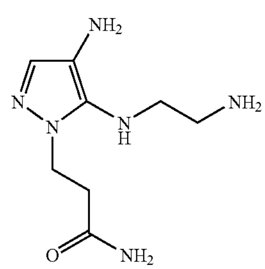 | 3-[4-amino-5-(2-amino-ethylamino)-pyrazol-1-yl]propion-amide | 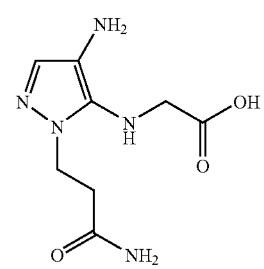 | [4-amino-2-(2-carbamoyl-ethyl)-2H-pyrazol-3-ylamino]-acetic acid |

-continued

| Structure | Name | Structure | Name | Structure | Name |
|---|---|---|---|---|---|
| 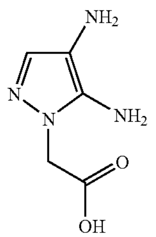 | (4,5-diamino-pyrazol-1-yl)acetic acid | 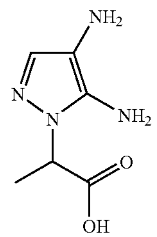 | 2-(4,5-diamino-pyrazol-1-yl)propionic acid | 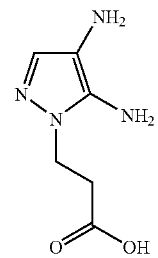 | 3-(4,5-diamino-pyrazol-1-yl)-propionic acid |
| 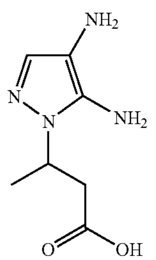 | 3-(4,5-diamino-pyrazol-1-yl)butyric acid | 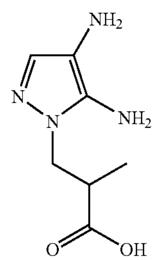 | 3-(4,5-diamino-pyrazol-1-yl)-2-methyl-propionic acid | 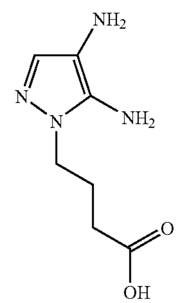 | 4-(4,5-diamino-pyrazol-1-yl)butyric acid |
| | 4-(4,5-diamino-pyrazol-1-yl)pentanoic acid | | 4-(4,5-diamino-pyrazol-1-yl)-3-methyl-butyric acid | | 4-(4,5-diamino-pyrazol-1-yl)-2-methyl-butyric acid |
| | 5-(4,5-diamino-pyrazol-1-yl)pentanoic acid | | 5-(4,5-diamino-pyrazol-1-yl)hexanoic acid | | 5-(4,5-diamino-pyrazol-1-yl)-4-methyl-pentanoic acid |
| 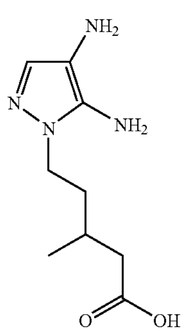 | 5-(4,5-diamino-pyrazol-1-yl)-3-methyl-pentanoic acid | 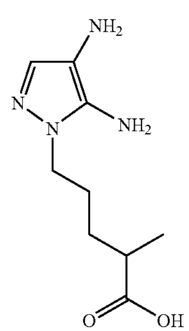 | 5-(4,5-diamino-pyrazol-1-yl)-2-methyl-pentanoic acid | 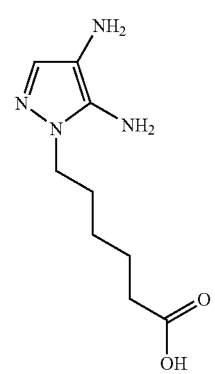 | 6-(4,5-diamino-pyrazol-1-yl)hexanoic acid |

-continued

| Structure | Name | Structure | Name | Structure | Name |
|---|---|---|---|---|---|
| 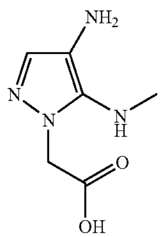 | (4-amino-5-methyl-amino-pyrazol-1-yl)acetic acid | 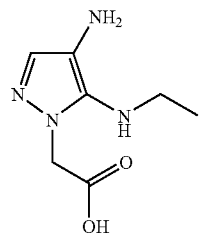 | (4-amino-5-ethylamino-pyrazol-1-yl)acetic acid | 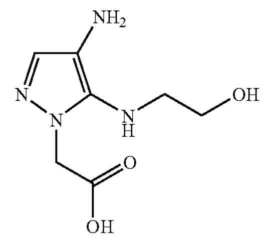 | [4-amino-5-(2-hydroxy-ethyl-amino)-pyrazol-1-yl]acetic acid |
| 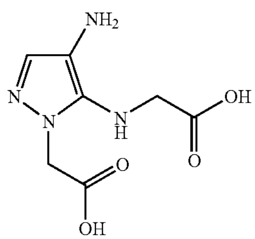 | [4-amino 5-(carboxy-methyl-amino)-pyrazol-1-yl]acetic acid | 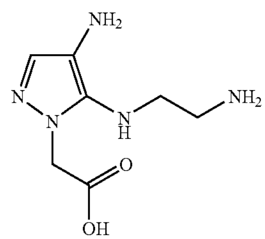 | [4-amino-5-(2-aminoethyl-amino)-pyrazol-1-yl]acetic acid | | |
| 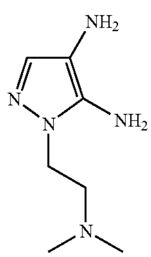 | 2-(2-dimethyl-amino-ethyl)-2H-pyrazole-3,4-diamine | 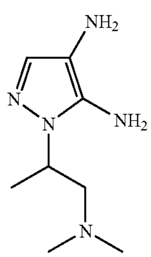 | 2-(2-dimethyl-amino-1-methyl-ethyl)-2H-pyrazol-3,4-diamine | 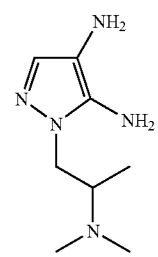 | 2-(2-dimethyl-amino-propyl)-2H-pyrazole-3,4-diamine |
| 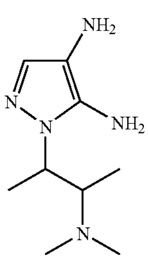 | 2-(2-dimethyl-amino-1-methyl-propyl)-2H-pyrazol-3,4-diamine | 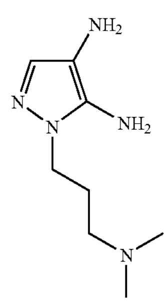 | 2-(3-dimethyl-amino-propyl)-2H-pyrazole-3,4-diamine | 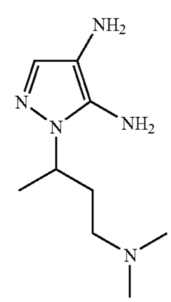 | 2-(3-dimethyl-amino-1-methyl-propyl)-2H-pyrazole-3,4-diamine |
| 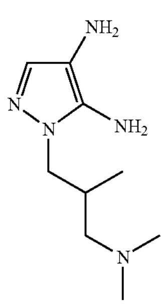 | 2-(3-dimethyl-amino-2-methyl-propyl)-2H-pyrazol-3,4-diamine | 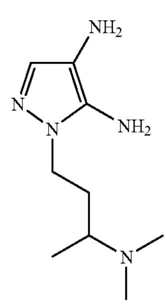 | 2-(3-dimethyl-aminobutyl)-2H-pyrazole-3,4-diamine | 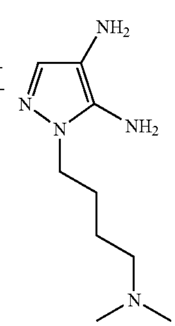 | 2-(4-dimethyl-amino-butyl)-2H-pyrazole-3,4-diamine |

-continued

| Structure | Name | Structure | Name | Structure | Name |
|---|---|---|---|---|---|
| 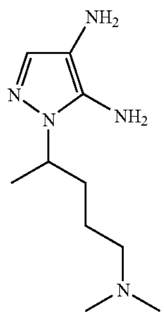 | 2-(4-dimethyl-amino-1-methyl-butyl)-2H-pyrazol-3,4-diamine | 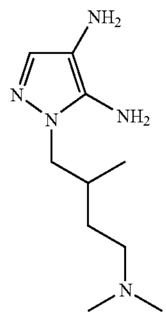 | 2-(4-dimethyl-amino-2-methyl-butyl)-2H-pyrazol-3,4-diamine | 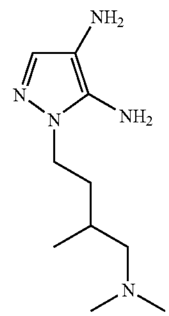 | 2-(4-dimethyl-amino-3-methyl-butyl)-2H-pyrazol-3,4-diamine |
| 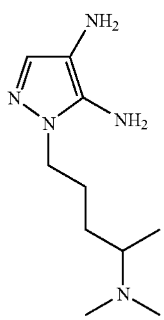 | 2-(4-dimethyl-amino-pentyl)-2H-pyrazole-3,4-diamine | 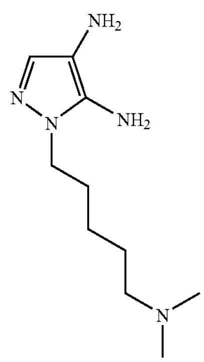 | 2-(5-dimethyl-amino-pentyl)-2H-pyrazole-3,4-diamine | 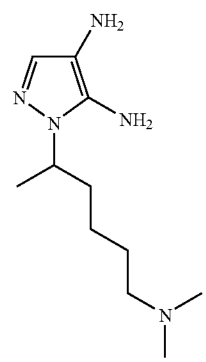 | 2-(5-dimethyl-amino-1-methyl-pentyl)-2H-pyrazole-3,4-diamine |
| 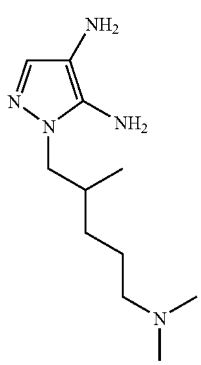 | 2-(5-dimethyl-amino-2-methyl-pentyl)-2H-pyrazole-3,4-diamine | 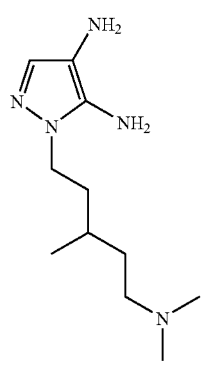 | 2-(5-dimethyl-amino-3-methyl-pentyl)-2H-pyrazole-3,4-diamine | 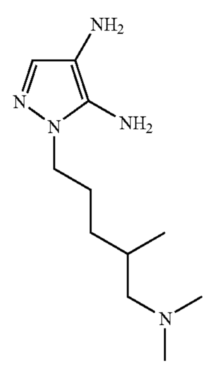 | 2-(5-dimethyl-amino-4-methyl-pentyl)-2H-pyrazole-3,4-diamine |
| | 2-(5-dimethyl-aminohexyl)-2H-pyrazole-3,4-diamine | | 2-(6-dimethyl-aminohexyl)-2H-pyrazole-3,4-diamine | | 2-(2-dimethyl-amino-ethyl)-N3-methyl-2H-pyrazole-3,4-diamine |

| Structure | Name | Structure | Name | Structure | Name |
|---|---|---|---|---|---|
| | 2-(2-dimethyl-amino-ethyl)-N3-ethyl-2H-pyrazole-3,4-diamine | | 2-[4-amino-2-(2-dimethyl-aminoethyl)-2H-pyrazol-3-ylamino]-ethanol | | 2-[4-amino-2-(2-dimethyl-aminoethyl)-2H-pyrazol-3-ylamino]-2H-pyrazole-3,4-dimaine | | 2-(2-dimethyl-amino-ethyl)-N3-(2-methoxy-ethyl)-2H-pyrazole-3,4-dimaine |
| | [4-amino-2-(2-dimethyl-aminoethyl)-2H-pyrazol-3-ylamino]-acetic acid | | N3-(2-amino-ethyl)-2-(2-dimethyl-aminoethyl)-2H-pyrazole-3,4-diamine | | 2-(3-dimethyl-amino-propyl)-N3-methyl-2H-pyrazole-3,4-diamine |
| 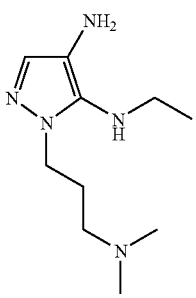 | 2-(3-dimethyl-amino-propyl)-N3-ethyl-2H-pyrazol-3,4-diamine | 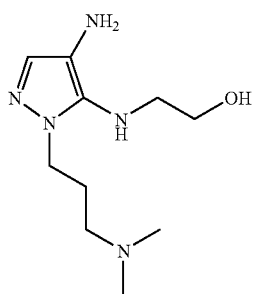 | 2-[4-amino-2-(3-di-methylamino-propyl)-2H-pyrazol-3-ylamino]-ethanol | 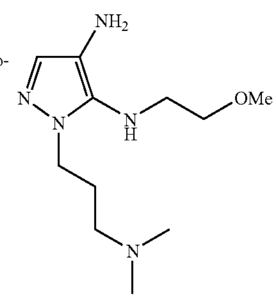 | 2-(3-dimethyyl-amino-propyl)-N3-(2-methoxy-ethyl)-2H-pyrazole-3,4-diamine |
| 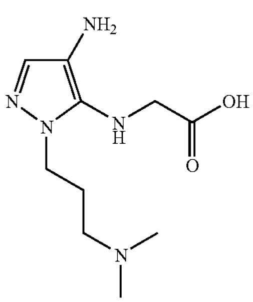 | [4-amino-2-(3-dimethyl-amino-propyl)-2H-pyrazol-3-ylamino]-acetic acid | 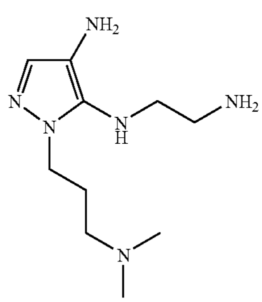 | N3-(2-aminoethyl)-2-(3-dimethyl-propyl)-2H-pyrazole-3,4-diamine | 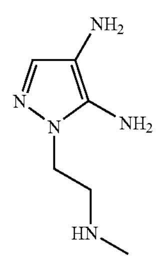 | 2-(2-methyl-amino-ethyl)-2H-pyrazole-3,4-diamine |
| 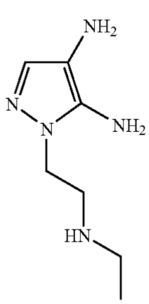 | 2-(2-ethyl-amino-ethyl)-2H-pyrazole-3,4-diamine | 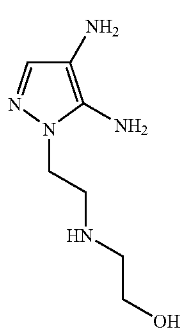 | 2-[2-(4,5-diamino-pyrazol-1-yl)ethyl-amino]-ethanol | 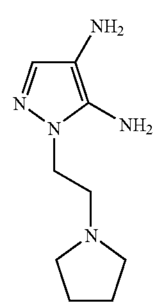 | 2-(2-pyrrolidin-1-ylethyl)-2H-pyrazole-3,4-diamine |

-continued

| Structure | Name | Structure | Name | Structure | Name |
|---|---|---|---|---|---|
| | 1-[2-(4,5-diamino-pyrazol-1-yl)ethyl]-pyrrolidin-3-ol | | 2-(2-imidazolidin-1-yl-ethyl)-2H-pyrazzole-3,4-diamine | | 2-(2-piperazin-1-ylethyl)-2H-pyrazole-3,4-diamine |
| 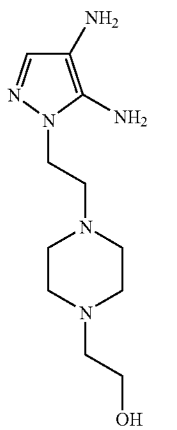 | 2-{4-[2-(4,5-diamino-pyrazol-1-yl)ethyl]-piperazin-1-yl}ethanol | 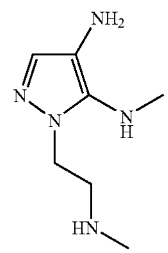 | N3-methyl-2-(2-methyl-aminoethyl)-2H-pyrazole-3,4-diamine | 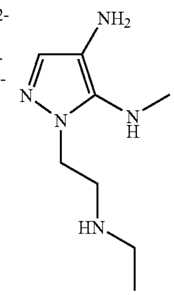 | 2-(2-ethyl-amino-ethyl)-N3-methyl-2H-pyrazole-3,4-diamine |
| 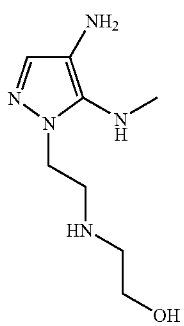 | 2-[2-(4-amino-5-methyl-amino-pyrazol-1-yl)ethyl-amino]-ethanol | 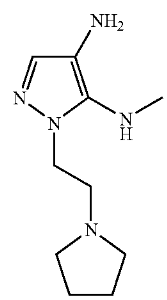 | N3-methyl-2-(2-pyrrolidin-1-ylethyl)-2H-pyrazole-3,4-diamine | 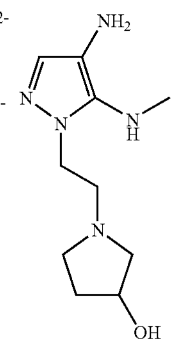 | 1-[2-(4-amino-5-methyl-amino-pyrazol-1-yl)ethyl]-pyrrolidin-3-ol |
| | 2-(2-imidazolidin-1-ylethyl)-N3-methyl-2H-pyrazole-3,4-diamine | | N3-methyl-2-(2-piperazin-1-ylethyl)-2H-pyrazole-3,4-diamine | | 2-{4-[2-(4-amino-5-methyl-amino-pyrazol-1-yl)ethyl]-piperazin-1-yl}ethanol |

| Structure | Name | Structure | Name | Structure | Name |
|---|---|---|---|---|---|
| 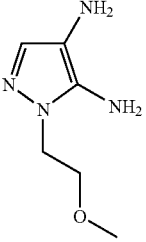 | 2-(2-methoxy-ethyl)-2H-pyrazole-3,4-diamine | 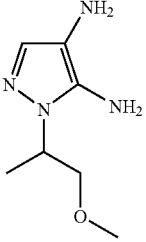 | 2-(2-methoxy-1-methyl-ethyl)-2H-pyrazole-3,4-diamine | 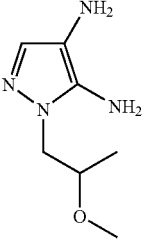 | 2-(2-methoxy-propyl)-2H-pyrazole-3,4-diamine |
| 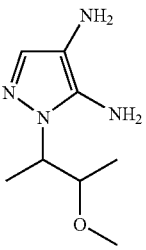 | 2-(2-methoxy-1-methyl-propyl)-2H-pyrazole-3,4-diamine | 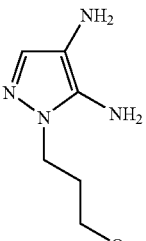 | 2-(3-methoxy-propyl)-2H-pyrazole-3,4-diamine | 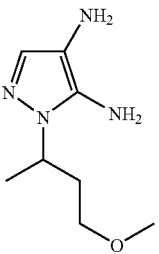 | 2-(3-methoxy-1-methyl-propyl)-2H-pyrazole-3,4-diamine |
| 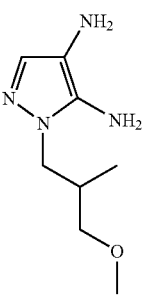 | 2-(3-methoxy-2-methyl-propyl)-2H-pyrazole-3,4-diamine | 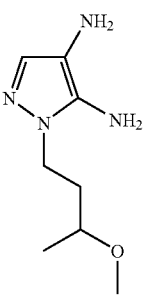 | 2-(3-methoxy-butyl-2H-pyrazole-3,4-diamine | 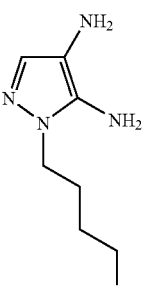 | 2-(4-methoxy-butyl)-2H-pyrazole-3,4-diamine |
| 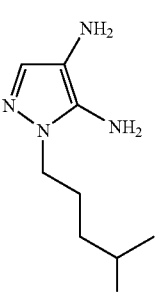 | 2-(4-Methoxy-1-methyl-butyl)-2H-pyrazole-3,4-diamine | 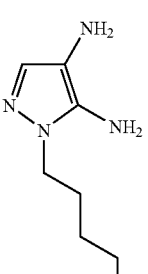 | 2-(4-Methoxy-2-methyl-butyl)-2H-pyrazole-3,4-dianmine | 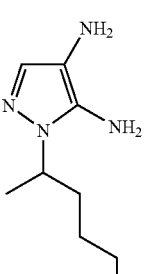 | 2-(4-Methoxy-3-methyl-butyl)-2H-pyrazole-3,4-diamine |
| 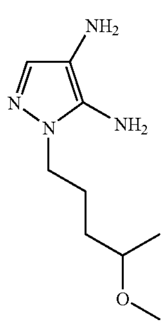 | 2-(4-Methoxy-pentyl)-2H-pyrazole-3,4-diamine | 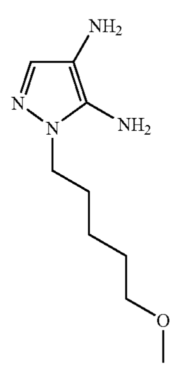 | 2-(5-Methoxy-pentyl)-2H-pyrazole-3,4-diamine | 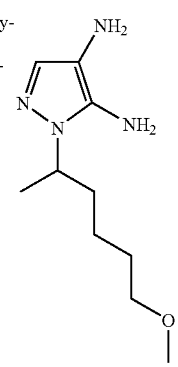 | 2-(5-Methoxy-1-methyl-pentyl)-2H-pyrazole-3,4-diamine |

| Structure | Name | Structure | Name | Structure | Name |
|---|---|---|---|---|---|
| 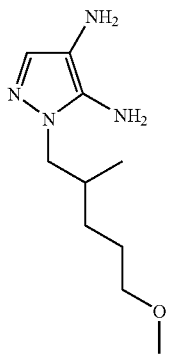 | 2-(5-Methoxy-2-methyl-pentyl)-2H-pyrazole-3,4-diamine | 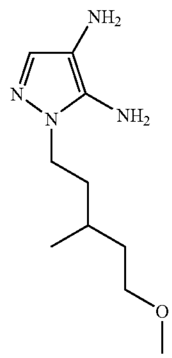 | 2-(5-Methoxy-3-methyl-pentyl)-2H-pyrazole-3,4-diamine | 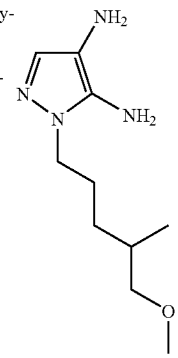 | 2-(5-Methoxy-4-methyl-pentyl)-2H-pyrazole-3,4-diamine |
| 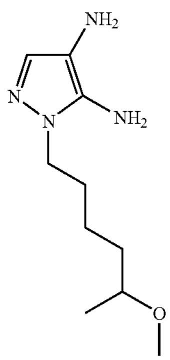 | 2-(5-Methoxy-hexyl)-2H-pyrazole-3,4-diamine | 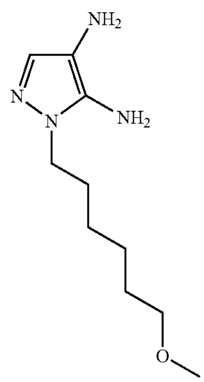 | 2-(6-Methoxy-hexyl)-2H-pyrazole-3,4-diamine | 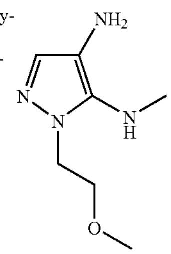 | 2-(2-Methoxy-ethyl)-N3-methyl-2H-pyrazole-3,4-diamine |
| 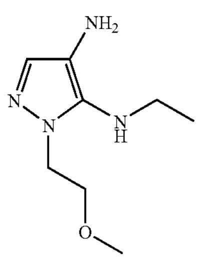 | N3-Ethyl-2-(2-methoxy-ethyl)-2H-pyrazole-3,4-diamine | 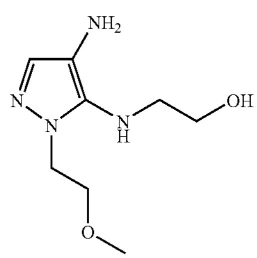 | 2-[4-Amino-2-(2-methoxy-ethyl)-2H-pyrazol-3-ylamino]-ethanol | 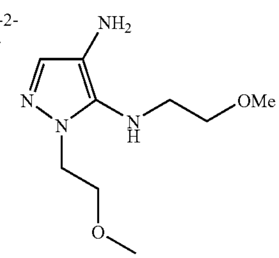 | 2,N3-Bis-2-(methoxy-ethyl)-2H-pyrazole-3,4-diamine |
| 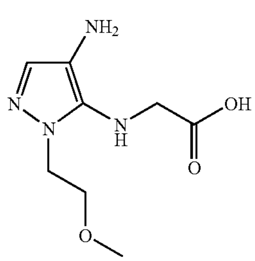 | [4-Amino-2-(2-methoxy-ethyl)-2H-pyrazol-3-ylamino]-acetique acide | 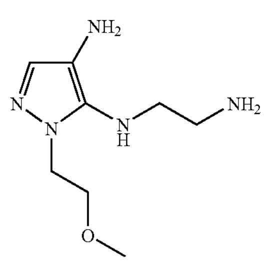 | N3-(2-Amino-ethyl)-2-(2-methoxy-ethyl)-2H-pyrazole-3,4-diamine | 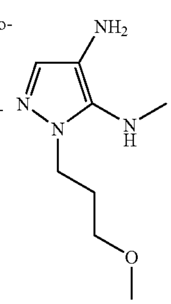 | 2-(3-Methoxy-propyl)-N3-methyl-2H-pyrazole-3,4-diamine |
| 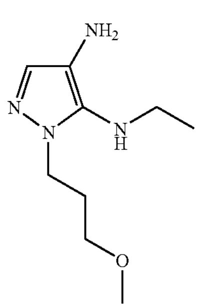 | N3-ethyl-2-(3-methoxypropyl)-2H-pyrazole-3,4-diamine | 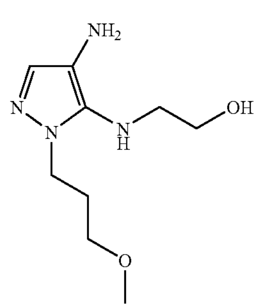 | 2-[4-amino-2-(3-methoxy-propyl)-2H-pyrazol-3-ylamino]-ethanol | 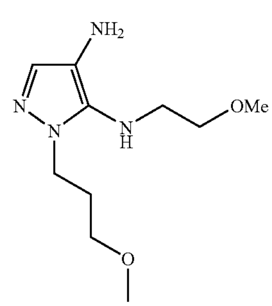 | N3-(2-methoxy-ethyl)-2-(3-methoxy-propyl)-2H-pyrazole-3,4-diamine |

-continued

| Structure | Name | Structure | Name | Structure | Name |
|---|---|---|---|---|---|
| 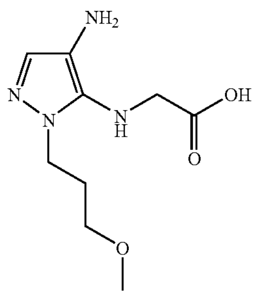 | [4-amino-2-(3-methoxy-propyl)-2H-pyrazol-3-ylamino]-acetic acid | 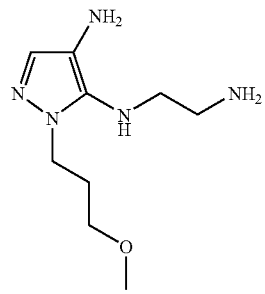 | N3-(2-amino-ethyl)-2-(3-methoxy-propyl)-2H-pyrazole-3,4-diamine | 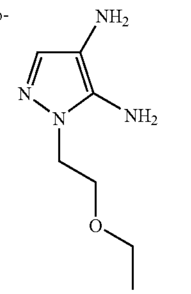 | 2-(2-ethoxy-ethyl)-2H-pyrazole-3,4-diamine |
| 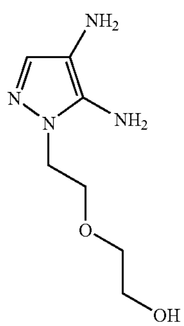 | 2-[2-(4,5-diamino-pyrazol-1-yl)ethoxy]ethanol | 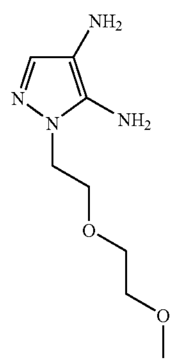 | 2-[2-(2-methoxy-ethoxy)-ethyl]-2H-pyrazole-3,4-diamine | 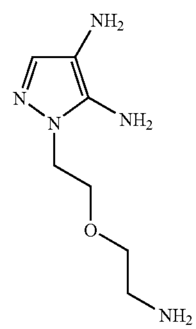 | 2-[2-(2-amino-ethoxy)-ethyl]-2H-pyrazole-3,4-diamine |
| 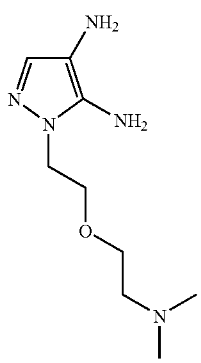 | 2-[2-(2-dimethyl-amino-ethoxy)-ethyl]-2H-pyrazole-3,4-diamine | 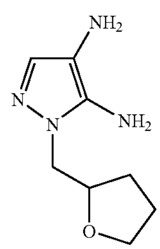 | 2-(tetra-hydrofuran-2-ylmethyl)-2H-pyrazole-3,4-diamine | 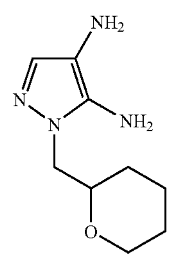 | 2-(tetra-hydropyran-2-ylmethyl)-2H-pyrazole-3,4-diamine |
| 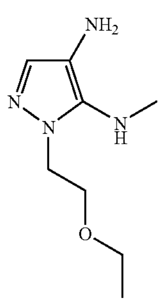 | 2-(2-ethoxy-ethyl)-N3-methyl-2H-pyrazole-3,4-diamine | 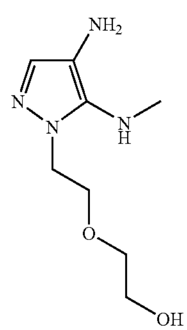 | 2-[2-(4-amino-5-methylamino-pyrazol-1-yl)ethoxy]ethanol | 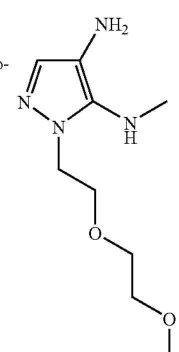 | 2-[2-(2-methoxy-ethoxy)-ethyl]-N3-methyl-2H-pyrazole-3,4-diamine |

| Structure | Name | Structure | Name | Structure | Name |
|---|---|---|---|---|---|
| 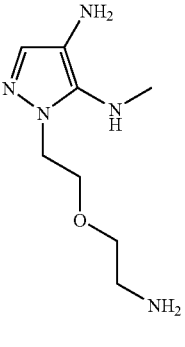 | 2-[2-(2-amino-ethoxy)-ethyl]-N3-methyl-2H-pyrazole-3,4-diamine | 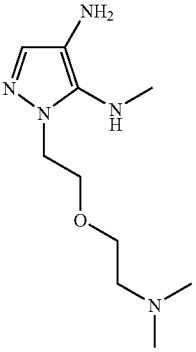 | 2-[2-(2-dimethyl-amino-ethoxy)-ethyl]-N3-methyl-2H-pyrazole-3,4-diamine | 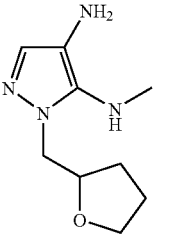 | N3-methyl-2-(tetra-hydrofuran-2-ylmethyl)-2H-pyrazole-3,4-diamine |
| 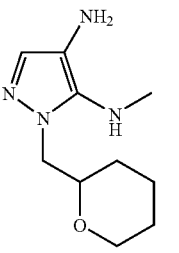 | N3-methyl-2-(tetrahydropyran-2-ylmethyl)-2H-pyrazole-3,4-diamine | | | | |

According to one preferred embodiment of the invention in formula (I), $R_1$ is a linear $C_1$-$C_3$ alkyl radical substituted with an $SO_3H$, COOH, $CONH_2$, methoxy, 2-hydroxyethyloxy, 2-hydroxyethylamino, mono- or dimethylamino, 1-pyrrolidinyl-3-ol, 1-imidazolidinyl, 1-piperazinyl, 1-piperazinylethanol, 2-tetrahydrofuryl or 2-tetrahydropyranyl group and $R_2$ denotes H, methyl, ethyl, 2-hydroxyethyl, 2-methoxyethyl, 2-aminoethyl or carboxymethyl.

The diaminopyrazoles of formula (I) that are preferred according to the invention have the following structures:

| Structure | Name | Structure | Name | Structure | Name |
|---|---|---|---|---|---|
| 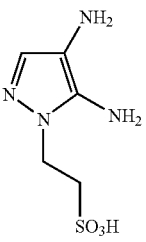 | 2-(4,5-diamino-pyrazol-1-yl)-ethane-sulfonic acid | 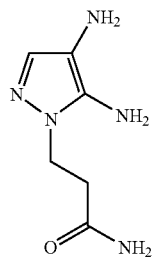 | 3-(4,5-diamino-pyrazol-1-yl)-propion-amide | 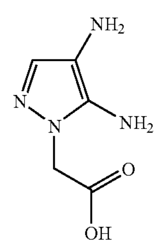 | (4,5-diamino-pyrazol-1-yl)-acetic acid |
| 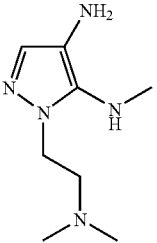 | 2-(2-dimethyl-amino-ethyl)-N3-methyl-2H-pyrazole-3,4-diamine | 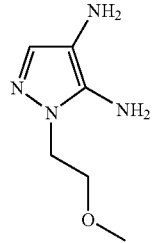 | 2-(2-methoxy-ethyl)-N3-methyl-2H-pyrazole-3,4-diamine | 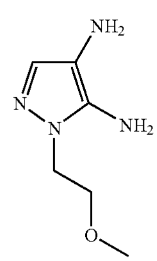 | 2-(2-methoxy-ethyl)-2H-pyrazole-3,4-diamine |

| Structure | Name | Structure | Name | Structure | Name |
|---|---|---|---|---|---|
| 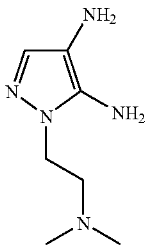 | 2-(2-dimethyl-amino-ethyl)-2H-pyrazole-3,4-diamine | | | 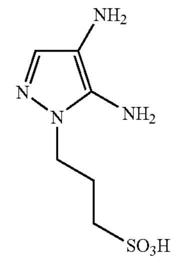 | 3-(4,5-diamino-pyrazol-1-yl)propane-1-sulfonic acid |
| 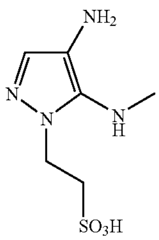 | 2-(4-amino-5-methyl-amino-pyrazol-1-yl)-ethane-sulfonic acid | 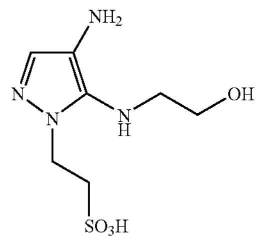 | 2-[4-amino-5-(2-hydroxy-ethyl-amino)-pyrazol-1-yl]-ethane-sulfonic acid | 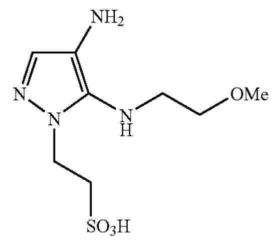 | 2-[4-amino-5-(2-methoxy-ethyl-amino)-pyrazol-1-yl]-ethane-sulfonic acid |
| 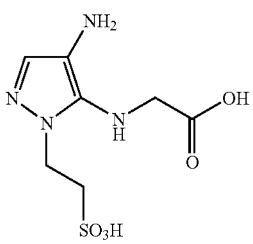 | [4-amino-2-(3-sulfo-propyl)-2H-pyrazol-3-yl-amino]-acetic acid | 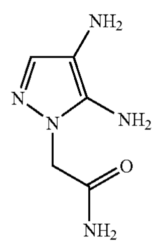 | 2-(4,5-diamino-pyrazol-1-yl)-acetamide | 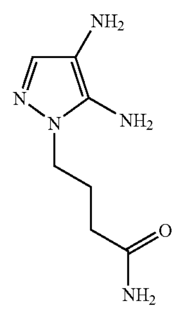 | 4-(4,5-diamino-pyrazol-1-yl)-butyr-amide |
| | 2-(4-amino-5-methyl-amino-pyrazol-1-yl)acet-amide | | 2-[4-amino-5-(2-hydroxy-ethyl-amino)-pyrazol-1-yl]-acetamide | | (4-amino-2-carba-moyl-methyl-2H-pyrazol-3-ylamino)-acetic acid |
| | 3-[4-amino-5-(2-amino-ethyl-amino)-pyrazol-1-yl]-propion-amide | | (4,5-diamino-pyrazol-1-yl)-acetic acid | | 3-(4,5-di-amino-pyrazol-1-yl)-propionic acid |
| 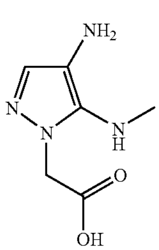 | (4-amino-5-methyl-amino-pyrazol-1-yl)-acetic acid | 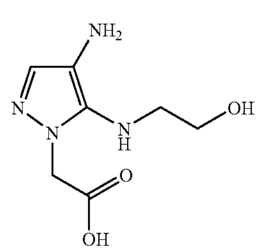 | [4-amino-5-(2-hydroxy-ethyl-amino)-pyrazol-1-yl]-acetic acid | 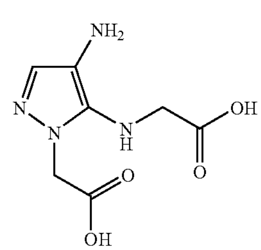 | [4-amino-5-(carboxy-methyl-amino)-pyrazol-1-yl]-acetic acid |

-continued

| Structure | Name | Structure | Name | Structure | Name |
|---|---|---|---|---|---|
| 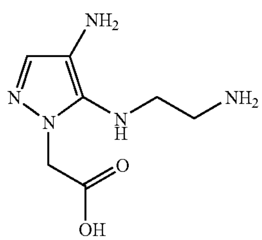 | [4-amino-5-(2-amino-ethyl-amino)-pyrazol-1-yl]-acetic acid | 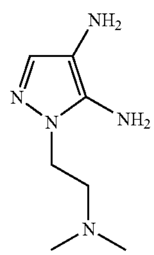 | 2-(2-dimethyl-amino-ethyl)-2H-pyrazole-3,4-diamine | 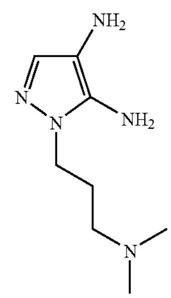 | 2-(3-dimethyl-amino-propyl)-2H-pyrazole-3,4-diamine |
| 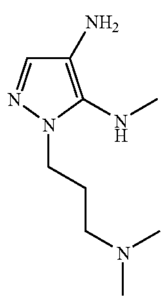 | 2-(3-dimethyl-amino-propyl)-N3-methyl-2H-pyrazole-3,4-diamine | 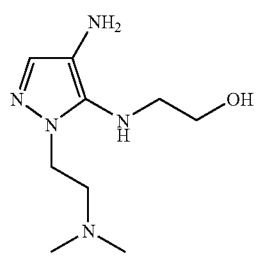 | 2-[4-amino-2-(2-dimethyl-amino-ethyl)-2H-pyrazol-3-ylamino]-ethanol | 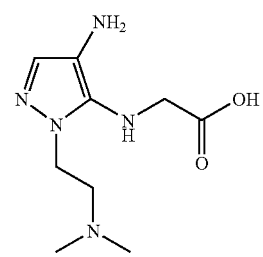 | [4-amino-2-(2-dimethyl-amino-ethyl)-2H-pyrazol-3-ylamino]-acetic acid |
| 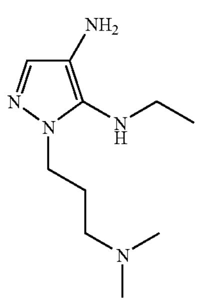 | 2-(3-dimethyl-amino-propyl)-N3-ethyl-2H-pyrazole-3,4-diamine | 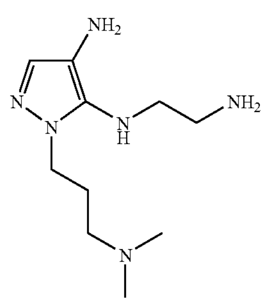 | N3-(2-amino-ethyl)-2-(3-dimethyl-amino-propyl)-2H-pyrazole-3,4-diamine | 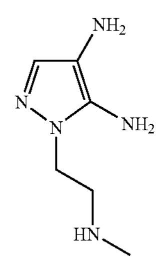 | 2-(2-methyl-amino-ethyl)-2H-pyrazole-3,4-diamine |
| 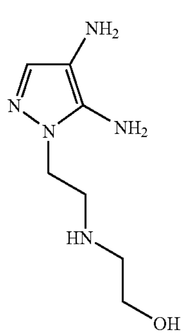 | 2-[2-(4,5-diamino-pyrazol-1-yl)-ethyl-amino]-ethanol | 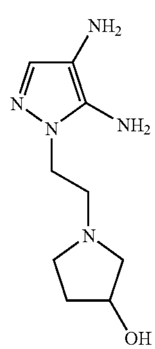 | 1-[2-(4,5-diamino-pyrazol-1-yl)-ethyl]-pyrrolidin-3-ol | 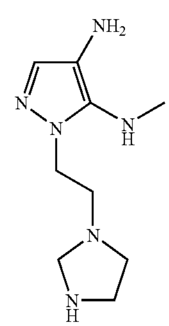 | 2-(2-imidazol-idin-1-ylethyl)-N3-methyl-2H-pyrazole-3,4-diamine |

| Name | Name | Name |
|---|---|---|
| N3-methyl-2-(2-piperazin-1-yl-ethyl)-2H-pyrazole-3,4-diamine | 2-{4-[2-(4-amino-5-methyl-amino-pyrazol-1-yl)-ethyl]-piperazin-1-yl}-ethanol | |
| 2-(3-methoxy-propyl)-2H-pyrazole-3,4-diamine | 2-(2-methoxy-ethyl)-N3-methyl-2H-pyrazole-3,4-diamine | 2-[4-amino-2-(2-methoxy-ethyl)-2H-pyrazol-3-ylamino]-ethanol |
| [4-amino-2-(2-methoxy-ethyl)-2H-pyrazol-3-ylamino]-acetic acid | N3-(2-methoxy-ethyl)-2-(3-methoxy-propyl)-2H-pyrazole-3,4-diamine | N3-(2-amino-ethyl)-2-(3-methoxy-propyl)-2H-pyrazole-3,4-diamine |
| 2-[2-(4,5-diamino-pyrazol-1-yl)-ethoxy]-ethanol | 2-[2-(2-methoxy-ethoxy)-ethyl]-2H-pyrazole-3,4-diamine | 2-[2-(2-amino-ethoxy)-ethyl]-2H-pyrazole-3,4-diamine |

-continued

| Structure | Name | Structure | Name | Structure | Name |
|---|---|---|---|---|---|
| 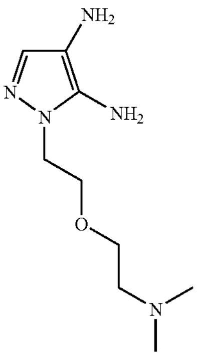 | 2-[2-(2-dimethyl-amino-ethoxy)-ethyl]-2H-pyrazole-3,4-diamine | 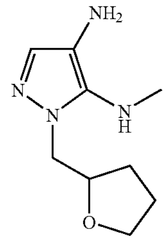 | N3-methyl-2-(tetra-hydro-furan-2-yl-methyl)-2H-pyrazole-3,4-diamine | 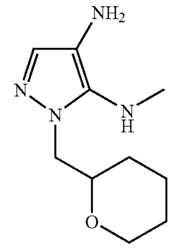 | N3-methyl-2-(tetra-hydro-pyran-2-yl-methyl)-2H-pyrazole-3,4-diamine |

The diaminopyrazoles of formula (I) that are more particularly preferred according to the invention are 4,5-diamino-1-(2'-methoxyethyl)pyrazole and 4-amino-1-(2'-methoxyethyl)-5-methylaminopyrazole, or the addition salts thereof with physiologically acceptable acids.

The diaminopyrazoles of formula (I) according to the invention are prepared, for example, according to the following general preparation method:

The synthetic approach shown below is described in the literature up to intermediate (2) (J. H. P. Juffermanns, C. L.; Habraken; J. Org. Chem., 1986, 51, 4656; Klebe et al., Synthesis, 1973, 294; R. Hüttel, F. Büchele; Chem. Ber., 1955, 88, 1586).

The alkylation and the amination to obtain the compounds of the type (5) of formula (I) according to the invention are mentioned in DE 42 34 885.

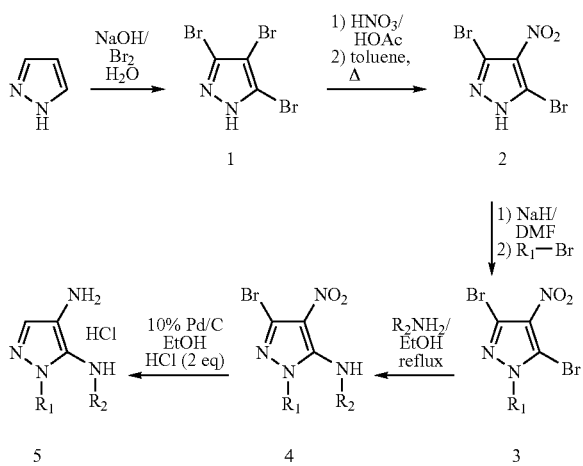

EXAMPLES OF THE SYNTHESIS

Synthesis of 3,4,5-tribromopyrazole (1)

NaOH (24 g, 0.6 mol) was added to an aqueous solution of pyrazole (10 g, 0.147 mol) with stirring (the temperature of the reaction medium is raised to 35° C.). After cooling the reaction medium to 20° C., Br$_2$ (72 g, 0.45 mol) was added dropwise over 1 hour, while maintaining the temperature between 20° C. and 25° C. The reaction was monitored by TLC (thin layer chromatography) (50% hexane/50% EtOAc or ethyl acetate). The precipitate was filtered off and washed with demineralized water (100 ml). The filtrate was acidified to pH 6-7 using HCl (10%, 33 g, 0.27 mol) and maintaining the temperature between 20 and 25° C. The precipitate thus formed was filtered off and washed with demineralized water (100 ml). The combined solids were maintained at reflux in Dean-Stark apparatus in the presence of toluene (200 ml). At the end of collection of the water, the organic phase was filtered while hot. The solvent was evaporated down to a residual volume of 110 ml. The solution was cooled to 0-5° C. for 1 hour. The precipitate formed was collected by filtration, washed with cold toluene (20 ml) and dried under vacuum at 80° C. to give the tribromide (1) in the form of an off-white solid (30 g, 67%).

NMR: $^{13}$C (100 MHz, d$_6$-DMSO): 97.7, 116.1, 126.4
IR (KBr; cm$^{-1}$): 3100, 2861, 1531, 1356, 1019, 969
m.p.: 182–184° C.

Synthesis of 3,5-dibromo-4-nitropyrazole (2)

HNO$_3$ (d=1.50 g/ml; 18 ml, 0.429 mol) was added dropwise over 10 minutes to a solution of 3,4,5-tribromopyrazole (50 g, 0.164 mol) in glacial acetic acid (750 ml) while maintaining the temperature at 15° C. Acetic anhydride (250 ml) was added and the reaction mixture was stirred at room temperature for 2 hours. Once the reaction was complete, the reaction mixture was poured onto crushed ice (1 kg). After stirring for 1 hour, the crude product was filtered off and then washed with demineralized water (2×60 ml) to give crude 1-nitro-3,4,5-tribromopyrazole. The water (24.6 ml) contained in the wet product was removed by heating a solution of the product in toluene (750 ml) at reflux in Dean-Stark apparatus. The toluene solution was maintained at reflux for a further 30 minutes until a TLC (eluent:toluene) showed that the rearrangement of the 1-nitro-3,4,5-tribromopyrazole (Rf=0.77), the intermediate formed, into 3,4,5-dibromo-4-nitropyrazole 2 (Rf=0.05) was complete. The solution was concentrated to a residual volume of 150 ml and then allowed to cool to 60° C., followed by addition of hexane (275 ml). The solution was cooled to 0-5° C. for 1 hour and the 3,5-dibromo-4-nitropyrazole 2 (29.1 g, 65%) was recovered by filtration and drying under vacuum in the form of a pale yellow solid.

| | |
|---|---|
| IR (KBr, cm$^{-1}$): | 3211, 1541, 1441, 1370, 1334, 976, 960, 824 |
| m.p.: | 127.6–130.1° C. |

General Method for Synthesizing the 1-alkyl-3,5-dibromo-4-nitropyrazole (3)

A solution of 3,5-dibromo-4-nitropyrazole (2) (1 mmol) in DMF (dimethylformamide) (4.8 ml) was added dropwise to a solution of NaH (1.1 mmol; 60% dispersion in oil, prewashed with hexane under an inert atmosphere) in DMF (8 ml) with stirring. An evolution of hydrogen gas took place. After 30 minutes, a solution of alkyl halide (1.2 mmol) in DMF (1.6 ml) was added dropwise over 10 minutes, followed by heating the reaction medium to 50-60° C. for 3 hours (monitored by TLC). The DMF was evaporated off under reduced pressure and the residue was taken up in a mixture of DCM (dichloromethane) (4 ml) and water (10 ml). The aqueous phase was extracted with DCM (3×10 ml) and the combined organic phases were washed with water (50 ml). The organic phase was dried over MgSO$_4$ and the solvent was evaporated off under reduced pressure to give the alkylated products of the type (3) in the form of oils or solids. The products were used without further purification in the amination step.

General Method for Synthesizing the 1-alkyl-5-alkylamino-3-bromo-4-nitropyrazole (4)

A mixture of 1-alkyl-3,5-dibromo-4-nitropyrazole (1 mmol) and alkylamine (14 mmol) in ethanol (25 ml) was refluxed for 4 hours (monitored by TLC). The ethanol and the excess alkylamine were evaporated off under reduced pressure. After trituration of the crude reaction mixtures with isopropyl ether, the compounds of the type (4) were obtained as solids.

Synthesis of 3-bromo-1-(2'-methoxyethyl)-5-methylamino4-nitropyrazole (compound of the type 4)

Aqueous 40% methylamine solution (300 ml, 8.71 mol) was added to a solution of 3,5-dibromo-1-(2'-methoxyethyl)$_4$-nitropyrazole (15 g, 0.483 mol) in ethanol (300 ml). The reaction mixture was stirred at 20-25° C. for 2 hours and then cooled to 0-5° C. for 30 minutes. The precipitate formed was filtered off and washed with a cold mixture of water/ethanol (1/1, 30 ml). The final amine product was obtained in the form of a yellow solid (4.6 g, 36%) after drying under reduced pressure.

| | |
|---|---|
| TLC (1/1: hexane/ethyl acetate): | R$_f$ = 0.31 |
| m.p.: | 154.4–156.8° C. |
| IR (KBr, cm$^{-1}$): | 3336, 1625, 1541, 1473, 1446, 1338, 1239, 1049, 839 |
| NMR: $^1$H (400MHz, d$_6$-DMSO): | 4.27(2H, t, J=5.0Hz, CH$_2$N), 3.74(2H, t, J=5.0Hz, CH$_2$O), 3.34(3H, s, OCH$_3$), 3.24(3H, d, J=5.5Hz, CH$_3$N). |

Synthesis of 3-bromo-1-(2'-methoxyethyl)-5-benzylamino-4-nitropyrazole (compound of the type 4)

The general method was applied using benzylamine.
The final amine product was recrystallized in an MeOH/H$_2$O mixture (1/1) and was isolated in the form of a yellow solid (48%).

| | |
|---|---|
| TLC (1/1: hexane/ethyl acetate): | R$_f$ = 0.46 |
| m.p.: | 91.1–93.8° C. |
| IR (KBr, cm$^{-1}$): | 3333, 1602, 1583, 1536, 1469, 1410, 1332, 1296, 1229, 1106, 1060, 732 |
| NMR: $^1$H (400MHz, CDCl$_3$): | 7.34(5H, m, H$_{arom}$), 4.77(2H, d, J=6.5Hz, NHC$\underline{H}_2$), 4.11(2H, t, J=5.0Hz, CH$_2$N), 3.71(2H, t, J=5.0Hz, CH$_2$O), 3.34(3H, s, OCH$_3$). |

4-Amino-1-(2'-methoxyethyl)-5-methylaminopyrazole dichlorohydrate (compound of the type 5) or (I)

A mixture of 3-bromo-1-(2'-methoxyethyl)-5-methylamino-4-pyrazole (5 g, 18 mmol) in ethanol (500 ml) containing 10% Pd/C catalyst (Johnson-Mattey Type 487, 0.5 g dry weight) and 36% hydrochloric acid (4.1 g, 40.4 mmol) was hydrogenated in a Parr autoclave (1 l) at 1.1 MPa for 3 hours (monitored by TLC). The catalyst was removed by filtration and washed with ethanol, and the filtrate was evaporated under reduced pressure. Under an inert atmosphere, the crude oil was taken up in ethanol (80 ml) and heated to 50° C. EtOAc (80 ml) was added and the mixture was maintained at room temperature for 3 hours and then cooled to 0-5° C. for 2 hours. The precipitate was recovered by filtration, washed with a cold mixture of EtOH/EtOAc (1/1, 2×30 ml) and dried under vacuum to give the final diamine dihydrochloride in the form of an off-white solid (4.1 g, 93%).

| Structure | Name |
|---|---|
| (pyrazole structure with NH$_2$, N-methyl, and 2-methoxyethyl groups) | 2-(2-Methoxyethyl)-N3-methyl-2H-pyrazole-3,4-diamine |

| Structure | Name |
|---|---|
| HPLC (purity): | 99.5% |
| TLC (MeOH): | $R_f$ = 0.57 (colorless spot turning red on contact with oxygen) |
| m.p.: | 157.6–159.8° C. |
| IR (KBr, cm$^{-1}$): | 3237, 3128, 2760, 2546, 1621, 1112 |
| NMR: $^1$H (400 MHz, d$_6$-DMSO): | 7.46 (1H, s, NH$_{arom}$), 4.10, (2H,m t, J = 5.5 Hz, CH$_2$N), 3.62 (2H, t, J = 5.5 Hz, CH$_2$O), 3.22 (3H, s, OCH$_3$), 2.84 (3H, s, NCH$_3$). |

4,5-Diamino-1-(2'-methoxyethyl)pyrazole dihydrochloride (compound of the type 5) or (I)

A mixture of 5-benzylamino-3-bromo-1-(2'-methoxyethyl)-4-nitropyrazole (4 g, 2.8 mmol) in ethanol (500 ml) containing 10% Pd/C catalyst (Johnson-Mattey type 487, 0.5 g dry weight) and 36% hydrochloric acid (0.57 g, 5.6 mmol) was hydrogenated in a Parr autoclave (1 l) at 1 MPa for 1 hour (monitored by TLC). The catalyst was removed by filtration and washed with ethanol, and the filtrate was evaporated under reduced pressure. A crude orange solid was obtained (2.8 g, 108%), which was triturated in EtOAc (20 ml) for 1 hour. The solid was filtered off and washed with cold EtOAc (20 ml) and then dried under vacuum to give the diamine (type 5) in the form of a beige-colored solid (0.7 g, 27%).

| Structure | Name |
|---|---|
| (structure: 2-(2-methoxyethyl)-2H-pyrazole-3,4-diamine) | 2-(2-Methoxyethyl)-2H-pyrazole-3,4-diamine |
| HPLC (purity): | 99.5% |
| TLC (MeOH): | $R_f$ = 0.48 (colorless spot turning red on contact with oxygen) |
| m.p.: | 168.1–173.0° C. |
| IR (KBr, cm$^-$): | 3309, 3158, 3050, 2892, 1647, 1619, 1587, 1504, 1422, 1344, 1281, 1111 |
| NMR: $^1$H (400 MHz, d$_6$-DMSO): | 7.34 (1H, s, NH$_{arom}$), 5.18 (1H, s$_{large}$, NH), 4.09 (2H, t, J = 5.5 Hz, CH$_2$N), 3.61 (2H, t, J = 5.5 Hz, CH$_2$O), 3.23 (3H, s, OCH$_3$). |

The dye composition according to the invention especially contains from 0.001% to 10% by weight, preferably from 0.05% to 6% by weight, and even more preferably from 0.1% to 3% by weight, of at least one diaminopyrazole of formula (I) or salts thereof.

The dye composition in accordance with the invention may also contain, in addition to the diaminopyrazole(s) defined above, at least one additional oxidation base that may be chosen from the oxidation bases conventionally used in oxidation dyeing and among which mention may be made especially of para-phenylenediamines, bis(phenyl)alkylenediamines, para-minophenols, ortho-aminophenols and heterocyclic bases other than the 4,5-diaminopyrazole used in accordance with the invention.

Among the para-phenylenediamines that may be mentioned more particularly, for example, are para-phenylenediamine, para-tolylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis (β-hydroxyethyl)-para-phenylenediamine, 4-amino-N-(β-methoxyethyl)aniline and the para-phenylenediamines described in French patent application FR 2 630 438, and the addition salts thereof.

Among the bis-phenylalkylenediamines that may be mentioned more particularly, for example, are N,N'-bis-(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(P-hydroxyethyl)-N,N'-bis(4-aminophenyl)tetramethylenediamine, N,N'-bis(4-methylaminophenyl)tetramethylenediamine and N,N'-bis (ethyl)-N,N'-bis(4'-amino-3'-methylphenyl) ethylenediamine, and the addition salts thereof.

Among the para-aminophenols that may be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof.

Among the ortho-aminophenols that may be mentioned more particularly, for example, are 2-aminophenol, 2-amino-5-methylphenol, 2-amino-6-methylphenol and 5-acetamido-2-aminophenol, and the addition salts thereof.

Among the heterocyclic bases that may be mentioned more particularly, for example, are pyridine derivatives, pyrimidine derivatives, pyrazole derivatives other than the diaminopyrazoles of formula (I) used in accordance with the invention, and the addition salts thereof.

When they are used, these additional oxidation bases preferably represent from 0.0005% to 12% by weight relative to the total weight of the dye composition and even more preferably from 0.005% to 6% by weight relative this weight.

The oxidation dye compositions in accordance with the invention may also contain at least one coupler and/or at least one direct dye, especially to modify the shades or to enrich them with glints.

The couplers that may be used in the oxidation dye compositions in accordance with the invention may be chosen from the couplers conventionally used in oxidation dyeing, and among which mention may be made especially of meta-phenylenediamines, metaminophenols, meta-diphenols, mono- or polyhydroxylated naphthalene derivatives and heterocyclic couplers such as, for example, indole or pyridine derivatives, and the addition salts thereof.

These couplers are chosen more particularly from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3- diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino) toluene, and the addition salts thereof.

When they are present, these couplers especially represent from 0.0001% to 10% of the total weight of the dye composition, preferably from 0.005% to 5% by weight 1 and even more preferably from 0.1% to 3% of this weight.

In general, the addition salts with an acid that may be used in the context of the dye compositions of the invention (oxidation bases and couplers) are chosen especially from the hydrochlorides, hydrobromides, sulfates, tartrates, lactates and acetates. The addition salts with a base are especially those obtained with sodium hydroxide, potassium hydroxide, ammonia, amines or alkanolamines.

The medium that is suitable for dyeing (or support) used according to the invention consists of water or of a mixture of water and at least one organic solvent chosen from $C_1$-$C_4$ lower alkanols, polyols and polyol ethers, aromatic alcohols, similar products and mixtures thereof.

The dye composition according to the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, reducing agents, sunscreens, penetrating agents, sequestering agents, fragrances, buffers, dispersants, conditioners, for instance silicones, film-forming agents, preserving agents and opacifiers.

The pH of the dye composition according to the invention is between 3 and 12.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The dye composition according to the invention may be in various forms, such as in the form of liquids, creams or gels, or in any other form that is suitable for dyeing keratin fibers, and especially human hair.

Another subject of the invention is a process for dyeing keratin fibers, and in particular human keratin fibers such as the hair, using the dye composition as defined above.

According to this process, at least one dye composition as defined above is applied to the fibers, for a time that is sufficient to develop the desired coloration, either in air or using an oxidizing agent. The dye composition may optionally contain oxidation catalysts, so as to accelerate the oxidation process.

According to a first embodiment of the process of the invention, the coloration of the fibers may be performed without adding an oxidizing agent, solely by contact with atmospheric oxygen.

According to a second embodiment of the process of the invention, at least one dye composition as defined above is applied to the fibers, the color being revealed at acidic, neutral or alkaline pH using an oxidizing agent that is added to the composition just at the time of use, or which is present in an oxidizing composition applied simultaneously or sequentially in a separate manner.

According to this second embodiment of the dyeing process of the invention, the dye composition described above is preferably mixed, at the time of use, with an oxidizing composition containing, in a medium that is suitable for dyeing, at least one oxidizing agent present in an amount that is sufficient to develop a coloration. The mixture obtained is than applied to the keratin fibers and is left for an action time of 3 to 50 minutes, and preferably 5 to 30 minutes, after which the fibers are rinsed, washed with shampoo, rinsed again and dried.

The oxidizing agent present in the oxidizing composition as defined above may be chosen from the oxidizing agents conventionally used for the oxidation dyeing of keratin fibers, and among which mention may be made of hydrogen peroxide, urea peroxide, alkali metal bromates and persalts such as perborates and persulfates. Hydrogen peroxide is particularly preferred.

The pH of the oxidizing composition containing the oxidizing agent as defined above is such that, after mixing with the dye composition, the pH of the resulting composition applied to the keratin fibers preferably ranges between 3 and 12, and even more preferably between 5 and 11. It is adjusted to the desired value by means of acidifying or basifying agents usually used in the dyeing of keratin fibers, and as defined above.

The oxidizing composition as defined above may also contain various adjuvants conventionally used in compositions for dyeing the hair and as defined above.

The composition that is finally applied to the keratin fibers may be in various forms, such as in the form of liquids, creams or gels, or in any other form that is suitable for dyeing keratin fibers, and especially human hair.

Another subject of the invention is a multi-compartment device or dyeing "kit" or any other multi-compartment packaging system, a first compartment of which contains the dye composition as defined above, and a second compartment of which contains the oxidizing composition as defined above. These devices may be equipped with a means for applying the desired mixture to the hair, such as the devices described in patent FR-2 586 913 in the name of the assignee.

The examples that follow are intended to illustrate the invention.

Examples 1 to 4 (Dyeing in Alkaline Medium)

The dye formulations below are prepared:

| | |
|---|---|
| 4,5-diaminopyrazole | $5 \times 10^{-3}$ mol |
| coupler | $5 \times 10^{-3}$ mol |
| oleyl alcohol polyglycerolated with 2 mol of glycerol | 4.0 g |
| oleyl alcohol polyglycerolated with 4 mol of glycerol, containing 78% active material (A.M.) | 5.7 g A.M. |
| oleic acid | 3.0 g |
| oleylamine containing 2 mol of ethylene oxide, sold under the trade name Ethomeen O12 by the company Akzo | 7.0 g |
| diethylaminopropyl laurylamino succinamate, sodium salt, at 55% A.M. | 3.0 g A.M. |
| oleyl alcohol | 5.0 g |
| oleic acid diethanolamide | 12.0 g |
| propylene glycol | 3.5 g |
| ethyl alcohol | 7.0 g |
| dipropylene glycol | 0.5 g |
| propylene glycol monomethyl ether | 9.0 g |

-continued

| | |
|---|---|
| sodium metabisulfite as an aqueous solution containing 35% A.M. | 0.455 g A.M. |
| ammonium acetate | 0.8 g |
| antioxidant, sequestering agent | qs |
| fragrance, preserving agent | qs |
| aqueous ammonia containing 20% NH$_3$ | 100 g | pH = 9.5
A.M. means "active material"

| DYEING AT ALKALINE pH | | |
|---|---|---|
| Example | Base | Coupler |
| 1 | 4,5-diamino-1-(2-methoxyethyl) pyrazole dihydrochloride | 6-chloro-2-methyl-5-aminophenol |
| 2 | 4,5-diamino-1-(2'-methoxyethyl) pyrazole dihydrochloride | 2,4-diamino-1-(β-hydroxyethyloxy)-benzene dihydrochloride |
| 3 | 4-amino-1-(2'-methoxyethyl)-5-methylaminopyrazole dihydrochloride | 6-chloro-2-methyl-5-aminophenol |
| 4 | 4-amino-1-(2'-methoxyethyl)-5-methylaminopyrazole dihydrochloride | 2,4-diamino-1-(β-hydroxyethyloxy)-benzene dihydrochloride |

At the time of use, each dye composition is mixed, weight for weight, with a 20-volumes aqueous hydrogen peroxide solution (6% by weight), the pH of which has been adjusted to about 2.5 with orthophosphoric acid.

The mixture is applied to natural or permanent-waved grey hair containing 90% white hairs, at a rate of 5 g per 0.5 g of hair, for 30 minutes.

The hair is then rinsed, washed with a standard shampoo and dried.

The color of the locks was evaluated in the L*a*b* system, on white and permanent-waved hair, using a Minolta CM 2002 spectrophotometer.

In the L*a*b* space, the lightness is indicated by the value L* on a scale from 0 to 100, while the shade and the saturation are expressed by a* and b*: a* and b* indicate two color axes, a* the red-green axis and b* the yellow-blue axis.

According to this system, the higher the value of L, the paler and less intense the color. Conversely, the lower the value of L, the darker or more intense the color.

| | Natural white hair | | | Permanent-waved white hair | | |
|---|---|---|---|---|---|---|
| Example | L* | a* | b* | L* | a* | b* |
| Example 1 | 39.47 | 30.8 | 16.2 | 33.62 | 32.8 | 17.29 |
| Example 2 | 25.86 | 23.5 | 0.93 | 19.29 | 19.0 | 1.35 |
| Example 3 | 36.43 | 28.3 | 1.48 | 29.32 | 30.3 | 1.98 |
| Example 4 | 25.75 | 14.8 | −8.36 | 19.53 | 13.2 | −8.02 |

The 4,5-diaminopyrazoles according to the invention thus make it possible to obtain strong and chromatic shades at alkaline pH.

Examples 5 AND 6 (Dyeing in Neutral Medium)

The same formulations as above are prepared, replacing the aqueous ammonia with citric acid in an amount such that the pH is equal to 7.

| DYEING AT NEUTRAL pH | | |
|---|---|---|
| Example | Base | Coupler |
| 5 | 4,5-diamino-1-(2'-methoxyethyl) pyrazole dihydrochloride | 2-methyl-5-aminophenol |
| 6 | 4,5-diamino-1-(2'-methoxyethyl) pyrazole dihydrochloride | 2-methyl-5-aminophenol |

Locks of natural and permanent-waved grey hair containing 90% white hairs are dyed with the dye compositions 5 and 6 above in the same manner as for the dyeing at alkaline pH.

The following shades are obtained:

| | Natural white hair | | | Permanent-waved white hair | | |
|---|---|---|---|---|---|---|
| Example | L | a* | b* | L* | a* | b* |
| Example 5 | 43.29 | 17.4 | 18.0 | 35.02 | 26.8 | 23.56 |
| Example 6 | 42.43 | 18.6 | 8.61 | 32.91 | 27.2 | 9.82 |

At neutral pH, the 4,5-diaminopyrazoles according to the invention make it possible to obtain strong shades.

The invention claimed is:

1. A diaminopyrazole derivative of the formula:

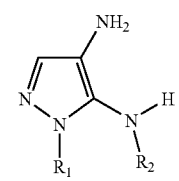

(I)

in which:
R$_1$ is a linear or branched C$_1$-C$_6$ alkyl radical, bearing at least one substituent which is OR, NHR, or NRR',
R and R', which may be identical or different, are a C$_2$-C$_4$ alkenyl radical,
R$_2$ denotes H or a linear or branched C$_1$-C$_6$ alkyl radical or C$_2$-C$_6$ alkenyl radical which is unsubstituted or substituted with one or more functional groups which are OH, NH$_2$, OR", NHR", NR"R'", SR", SOR", SO$_2$R", COOH, CONH$_2$, CONR"R'", PO(OH)$_2$, SH, SO$_3$X, a non-cationic heterocycle, Cl, Br or I, X, R and R' being defined as above,
R" and R'", which may be identical or different, are a linear or branched C$_1$-C$_6$ alkyl radical or C$_2$-C$_6$ alkenyl radical,
or a physiologically acceptable salt thereof.

2. A diaminopyrazole derivative of the formula:

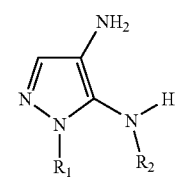

(I)

in which:
- $R_1$ is a linear or branched $C_1$-$C_6$ alkyl radical, bearing at least one substituent which is OR, NHR, or NRR',
- R and R', which may be identical or different, are a linear or branched $C_1$-$C_6$ alkyl radical or $C_2$-$C_6$ alkenyl radical which is unsubstituted or substituted with one or more functional groups which are OH, $NH_2$, OR", NHR", NR"R'", SR", SOR", $SO_2R$", COOH, $CONH_2$, CONR"R'", $PO(OH)_2$, SH, $SO_3X$, a non-cationic heterocycle, Cl, Br or I, X being H, Na, K or $NH_4$,
- $R_2$ is a $C_2$-$C_4$ alkenyl radical,
- R" and R'", which may be identical or different, are a linear or branched $C_1$-$C_6$ alkyl radical or $C_2$-$C_6$ alkenyl radical or a physiologically acceptable salt thereof.

3. A physiologically acceptable salt of a diaminopyrazole derivative of the formula:

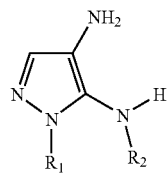

(I)

in which:
- $R_1$ is a linear or branched $C_1$-$C_6$ alkyl radical, bearing at least one substituent which is OR, NHR, or NRR',
- R and R', which may be identical or different, are a linear or branched $C_1$-$C_6$ alkyl radical or $C_2$-$C_6$ alkenyl radical which is unsubstituted or substituted with one or more functional groups which are OH, $NH_2$, OR", NHR", NR"R'", SR", SOR", $SO_2R$", COOH, $CONH_2$, CONR"R'", $PO(OH)_2$, SH, $SO_3X$, a non-cationic heterocycle, Cl, Br or I, X being H, Na, K or $NH_4$,
- $R_2$ denotes H or a linear or branched $C_1$-$C_6$ alkyl radical or $C_2C_6$ alkenyl radical which is unsubstituted or substituted with one or more functional groups which are OH, $NH_2$, OR", NHR", NR"R'", SR", SOR", $SO_2R$", COOH, $CONH_2$, CONR"R'", $PO(OH)_2$, SH, $SO_3X$, a non-cationic heterocycle, Cl, Br or I, X, R and R' being defined as above, R" and R'", which may be identical or different, are a linear or branched $C_1$-$C_6$ alkyl radical or $C_2$-$C_6$ alkenyl radical, wherein the physiologically acceptable salt is an acid salt which is a hydrochloride, hydrobromide, sulfate, tartrate, lactate or acetate, or a salt of a base which is sodium hydroxide, potassium hydroxide, ammonia, an amine or an alkanolamine.

4. The diaminopyrazole chosen from 4,5-diamino-1-(2'-methoxyethyl)pyrazole or 4-amino-1-(2'-methoxyethyl)-5-methylaminopyrazole, or a salt thereof with a physiologically acceptable acid.

5. A composition for the oxidation dyeing of human keratin fibers, comprising, in a medium for dyeing, as an oxidation base, at least one 4,5-diaminopyrazole of

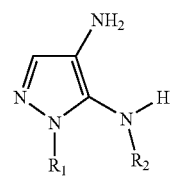

(I)

in which:
- $R_1$ is a linear or branched substituted $C_2$-$C_4$ alkenyl radical,
- $R_2$ is H or a linear or branched $C_1$-$C_6$ alkyl radical or $C_2$-$C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I,
- wherein X is H, Na, K, $NH_4$ and R and R', which may be identical or different, are a linear or branched $C_1$-$C_6$ alkyl radical or $C_2$-$C_6$ alkenyl radical, which is unsubstituted or substituted with one or more functional groups which are OH, $NH_2$, OR, NHR, NRR', SR, SOR, $SO_2R$, COOH, $CONH_2$, CONRR'$PO(OH)_2$, SH, $SO_3X$, a non-cationic heterocycle, Cl Br or,
- or an addition salt thereof with a physiologically acceptable acid or base.

6. A composition for the oxidation dyeing of human keratin fibers, comprising, in a medium for dyeing, as an oxidation base, at least one 4,5-diaminopyrazole of formula (I):

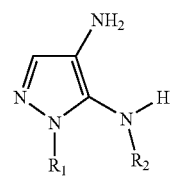

(I)

in which:
- $R_1$ is a linear or branched $C_1$-$C_6$ alkyl radical or $C_2$-$C_6$ alkenyl radical, bearing at least one substituent which is OR, NHR, NRR', SR, SOR, $SO_2R$, COOH, $CONH_2$, CONRR', $PO(OH)_2$, SH, $SO_3X$, a non-cationic heterocycle, Cl, Br or I,
- X is H, Na, K or $NH_4$,
- R and R', which may be identical or different, are a $C_2$-$C_4$ alkenyl radical,
- $R_2$ is H or a linear or branched $C_1$-$C_6$ alkyl radical or $C_2C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, SO3X, a non-cationic heterocycle, Cl, Br or I, X, R and R' being defined as above,
- or an addition salt thereof with a physiologically acceptable acid or base.

7. A composition for the oxidation dyeing of human keratin fibers, comprising, in a medium for dyeing, as an oxidation base, at least one 4,5-diaminopyrazole of formula (I):

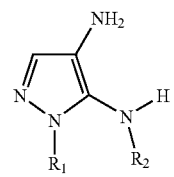

(I)

in which:
- $R_1$ is a linear or branched $C_1$-$C_6$ alkyl radical or $C_2$-$C_6$ alkenyl radical, bearing at least one substituent which is OR, NHR, NRR', SR, SOR, SO$_2$R, COGH, COOH$_2$, CONRR', PO(OH)$_2$, SH, SO$_3$X, a non-cationic heterocycle, Cl, Br or I, X is H, Na, K or NH$_4$, R and R', which may be identical or different, are a linear or branched C$_1$-C$_6$ alkyl radical or C$_2$-C$_6$ alkenyl radical, which is unsubstituted or substituted with one or more functional groups which are OH, NH$_2$, OR, NHR, NRR', SR, SOR, SO$_2$R, COOH, CONH$_2$, CONRR', PO(OH)$_2$, SH, SO$_3$X, a non-cationic heterocycle, Cl, Br or I, X being defined as above, R$_2$ is C$_2$-C$_4$ alkenyl radical, or an addition salt thereof with a physiologically acceptable acid or base.

8. A composition for the oxidation dyeing of human keratin fibers, comprising, in a medium for dyeing, as an oxidation base, at least one 4,5-diaminopyrazole of formula (I):

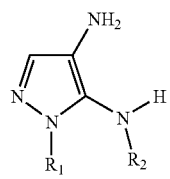

(I)

in which:

R$_1$ is a linear or branched C$_1$-C$_6$ alkyl radical or C$_2$-C$_6$ alkenyl radical, bearing at least one substituent which is OR, NHR, NRR', SR, SOR, SO$_2$R, COOH, CONH$_2$, CONRR', PO(OH)$_2$, SH, SO$_3$X, a non-cationic heterocycle, Cl, Br or I, X is H, Na, K or NH$_4$, R and R', which may be identical or different, are a linear or branched C$_1$-C$_6$ alkyl radical or C$_2$-C$_6$ alkenyl radical, which is unsubstituted or substituted with one or more functional groups which are OH, NH$_2$, OR, NHR, NRR', SR, SOR, SO$_2$R, COOH, CONH$_2$, CONRR', PO(OH)$_2$, SH, SO$_3$X, a non-cationic heterocycle, Cl, Br or I, X being defined as above, R$_2$ is H or a linear or branched C$_1$-C$_6$ alkyl radical or C$_2$-C$_6$ alkenyl radical, which is unsubstituted or substituted with one or more functional groups which are OH, NH$_2$, OR, NHR, NRR', SR, SOR, SO$_2$R, COOH, CONH$_2$, CONRR', PO(OH)$_2$, SH, SO$_3$X, a non-cationic heterocycle, Cl, Br or I, X, R and R' being defined as above, or an addition salt thereof with a physiologically acceptable acid or base, wherein the composition contains from 0.001% to 10% by weight of at least one diaminopyrazole of formula (I) or a salt thereof.

9. The composition as claimed in claim 8, wherein the composition contains from 0.05% to 6% by weight of at least one diaminopyrazole of formula (I) or a salt thereof.

10. The composition as claimed in claim 8, wherein the composition contains from 0.1% to 3% by weight of at least one diaminopyrazole of formula (I) or a salt thereof.

11. A composition for the oxidation dyeing of human keratin fibers, comprising, in a medium for dyeing, as an oxidation base, at least one 4,5-diaminopyrazole of formula (I):

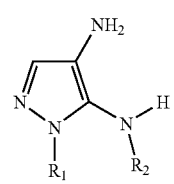

(I)

in which:

R$_1$ is a linear or branched C$_1$-C$_6$ alkyl radical or C$_2$-C$_6$ alkenyl radical, bearing at least one substituent which is OR, NHR, NRR', SR, SOR, SO$_2$R, COOH, CONH$_2$, CONRR', PO(OH)$_2$, SH, SO$_3$X, a non-cationic heterocycle, Cl, Br or I, X is H, Na, K or NH$_4$, R and R', which may be identical or different, are a linear or branched C$_1$-C$_6$ alkyl radical or C$_2$-C$_6$ alkenyl radical, which is unsubstituted or substituted with one or more functional groups which are OH, NH$_2$, OR, NHR, NRR', SR, SOR, SO$_2$R, COOH, CONH$_2$, CONRR', PO(OH)$_2$, SH, SO$_3$X, a non-cationic heterocycle, Cl, Br or I, X being defined as above, R$_2$ is H or a linear or branched C$_1$-C$_6$ alkyl radical or C$_2$C$_6$ alkenyl radical, which is unsubstituted or substituted with one or more functional groups which are OH, NH$_2$, OR, NHR, NRR', SR, SOR, SO$_2$R, COOH, CONH$_2$, CONRR', PO(OH)$_2$, SH, SO$_3$X, a non-cationic heterocycle, Cl, Br or I, X, R and R' being defined as above, or an addition salt thereof with a physiologically acceptable acid or base, wherein the medium for dyeing consists of water or a mixture of water and at least one organic solvent which is a C$_1$-C$_4$ lower alkanol, polyol or polyol ether, aromatic alcohol, or a mixture thereof.

12. A composition for the oxidation dyeing of human keratin fibers, comprising, in a medium for dyeing, as an oxidation base, at least one 4,5-diaminopyrazole of formula (I):

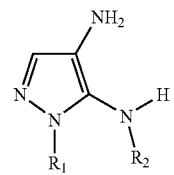

(I)

in which:

R$_1$ is a linear or branched C$_1$-C$_6$ alkyl radical or C$_2$-C$_6$ alkenyl radical, bearing at least one substituent which is OR, NHR, NRR', SR, SOR, SO$_2$R, COOH, CONH$_2$, CONRR', PO(OH)$_2$, SH, SO$_3$X, a non-cationic heterocycle, Cl, Br or I, X is H, Na, K or NH$_4$, R and R', which may be identical or different, are a linear or branched C$_1$-C$_6$ alkyl radical or C$_2$-C$_6$ alkenyl radical, which is unsubstituted or substituted with one or more functional groups which are OH, NH$_2$, OR, NHR, NRR', SR, SOR, SO$_2$R, COOH, CONH$_2$, CONRR', PO(OH)$_2$, SH, SO$_3$X, a non-cationic heterocycle, Cl, Br or I, X being defined as above, R$_2$ is H or a linear or branched C$_1$-C$_6$ alkyl radical or C$_2$C$_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X, R and R' being defined as above, or an addition salt thereof with a physiologically acceptable acid or base, wherein the composition has a pH of between 3 and 12.

13. A composition for the oxidation dyeing of human keratin fibers, comprising, in a medium for dyeing, as an oxidation base, at least one 4,5-diaminopyrazole of formula (I):

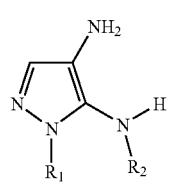

in which:
- $R_1$ is a linear or branched $C_1$-$C_6$ alkyl radical or $C_2$-$C_6$ alkenyl radical, bearing at least one substituent which is OR, NHR, NRR', SR, SOR, $SO_2R$, COOH, $CONH_2$, CONRR', $PO(OH)_2$, SH, $SO_3X$, a non-cationic heterocycle, Cl, Br or I,
- X is H, Na, K or $NH_4$,
- R and R', which may be identical or different, are a linear or branched $C_1$-$C_6$ alkyl radical or $C_2$-$C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X being defined as above, $R_2$ is H or a linear or branched $C_1$-$C_6$ alkyl radical or $C_2C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X, R and R' being defined as above, or an addition salt thereof with a physiologically acceptable acid or base, wherein the composition contains at least one additional oxidation base that is a para-phenylenediamine, bis(phenyl)alkylenediamine, para-aminophenol, ortho-aminophenol or heterocyclic base other than a diaminopyrazole of formula (I), or an addition salt thereof with an acid.

14. The composition as claimed in claim 13, wherein the additional oxidation base comprises from 0.0005% to 12% by weight relative to the total weight of the composition.

15. A composition for the oxidation dyeing of human keratin fibers, comprising, in a medium for dyeing, as an oxidation base, at least one 4,5-diaminopyrazole of formula (I):

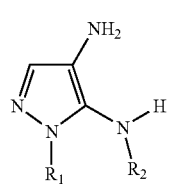

in which:
- $R_1$ is a linear or branched $C_1$-$C_6$ alkyl radical or $C_2$-$C_6$ alkenyl radical, bearing at least one substituent which is OR, NHR, NRR', SR, SOR, $SO_2R$, COOH, $CONH_2$, CONRR', $PO(OH)_2$, SH, $SO_3X$, a non-cationic heterocycle, Cl, Br or I,
- X is H, Na, K or $NH_4$,
- R and R', which may be identical or different, are a linear or branched $C_1$-$C_6$ alkyl radical or $C_2$-$C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X being defined as above,
- $R_2$ is H or a linear or branched $C_1$-$C_6$ alkyl radical or $C_2$-$C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X, R and R' being defined as above, or an addition salt thereof with a physiologically acceptable acid or base, wherein the composition contains at least one coupler and/or at least one direct dye.

16. The composition as claimed in claim 15, wherein the coupler is meta-phenylenediamine, meta-aminophenol, meta-diphenol, a mono- or polyhydroxylated naphthalene derivative or a heterocyclic coupler, or an addition salt thereof with an acid.

17. The composition as claimed in claim 15, wherein the coupler comprises from 0.0001% to 10% by weight relative to the total weight of the composition.

18. A composition for the oxidation dyeing of human keratin fibers, comprising, in a medium for dyeing, as an oxidation base, at least an addition salt of one 4,5-diaminopyrazole of formula (I):

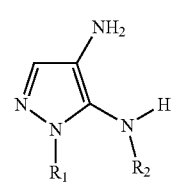

in which:
- $R_1$ is a linear or branched $C_1$-$C_6$ alkyl radical or $C_2$-$C_6$ alkenyl radical, bearing at least one substituent which is OR, NHR, NRR', SR, SOR, $SO_2R$, COOH, $CONH_2$, CONRR', $PO(OH)_2$, SH, $SO_3X$, a non-cationic heterocycle, Cl, Br or I,
- X is H, Na, K or $NH_4$,
- R and R', which may be identical or different, are a linear or branched $C_1$-$C_6$ alkyl radical or $C_2$-$C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X being defined as above,
- $R_2$ is H or a linear or branched $C_1$-$C_6$ alkyl radical or $C_2C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X, R and R' being defined as above, wherein the addition salt with an acid is a hydrochloride, hydrobromide, sulfate, tartrate, lactate or acetate and the addition salt with a base is sodium hydroxide, potassium hydroxide, ammonia or an amine with a physiologically acceptable acid or base.

19. A process for dyeing human keratin fibers, comprising applying at least one dye composition for the oxidation dyeing of human keratin fibers, comprising, in a medium for dyeing, as an oxidation base, at least one 4,5-diaminopyrazole of formula (I):

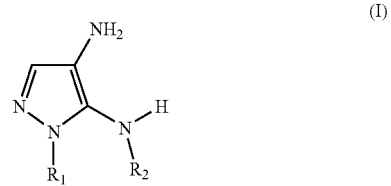

in which:
- $R_1$ is a linear or branched $C_1$-$C_6$ alkyl radical or $C_2$-$C_6$ alkenyl radical, bearing at least one substituent which is OR, NHR, NRR', SR, SOR, $SO_2R$, COOH, $CONH_2$, CONRR', $PO(OH)_2$, SH, $SO_3X$, a non-cationic heterocycle, Cl, Br or I,
- X is H, Na, K or $NH_4$,
- R and R', which may be identical or different, are a linear or branched $C_1$-$C_6$ alkyl radical or $C_2$-$C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X being defined as above,
- $R_2$ is H or a linear or branched $C_1$-$C_6$ alkyl radical or $C_2C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X, R and R' being defined as above, or an addition salt thereof with a physiologically acceptable acid or base to the fibers for a time sufficient to develop a coloration, either in air or in the presence of an oxidizing agent, and optionally in the presence of an oxidation catalyst.

20. The process as claimed in claim 19, wherein the coloration is developed solely by contact with atmospheric oxygen.

21. The process as claimed in claim 19, wherein the color is developed at an acidic, neutral or alkaline pH with the aid of an oxidizing agent which is added to the dye composition at the time of use or which is present in an oxidizing composition applied simultaneously or sequentially in a separate step.

22. The process as claimed in claim 19, wherein the oxidizing agent is hydrogen peroxide, urea peroxide, an alkali metal bromate or persalt.

23. The process as claimed in claim 22, wherein the persalt is perborate or persulfate.

24. A multi-compartment device or multi-compartment dyeing kit, comprising a first compartment containing a dye composition for dyeing human keratin fibers comprising, in a medium for dyeing, as an oxidation base, at least one 4,5-diaminopyrazole of formula (I):

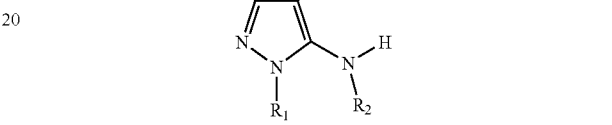

in which:
- $R_1$ is a linear or branched $C_1$-$C_6$ alkyl radical or $C_2$-$C_6$ alkenyl radical, bearing at least one substituent which is OR, NHR, NRR', SR, SOR, $SO_2R$, COOH, $CONH_2$, CONRR', $PO(OH)_2$, SH, $SO_3X$, a non-cationic heterocycle, Cl, Br or I,
- X is H, Na, K or $NH_4$,
- R and R', which may be identical or different, are a linear or branched $C_1$-$C_6$ alkyl radical or $C_2$-$C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X being defined as above,
- $R_2$ is H or a linear or branched $C_1$-$C_6$ alkyl radical or $C_2C_6$ alkenyl radical, which is unsubstituted or substituted with one or more functional groups which are OH, $NH_2$, OR, NHR, NRR', SR, SOR, $SO_2R$, COOH, $CONH_2$, CONRR', $PO(OH)_2$, SH, $SO_3X$, a non-cationic heterocycle, Cl, Br or I, X, R and R' being defined as above, or an addition salt thereof with a physiologically acceptable acid or base, and a second compartment containing an oxidizing composition.

* * * * *